US011685945B2

(12) United States Patent
Tucker

(10) Patent No.: US 11,685,945 B2
(45) **Date of Patent: *Jun. 27, 2023**

(54) ENZYME ASSAY WITH DUPLICATE FLUOROPHORES

(71) Applicant: BIOMADISON, INC., Del Mar, CA (US)

(72) Inventor: Ward C Tucker, Monona, WI (US)

(73) Assignee: BioMadison, Inc., Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/784,121

(22) Filed: Feb. 6, 2020

(65) Prior Publication Data

US 2021/0032675 A1 Feb. 4, 2021

Related U.S. Application Data

(62) Division of application No. 14/523,712, filed on Oct. 24, 2014, now abandoned.

(60) Provisional application No. 62/058,532, filed on Oct. 1, 2014, provisional application No. 62/014,586, filed on Jun. 19, 2014, provisional application No. 61/897,352, filed on Oct. 30, 2013, provisional application No. 61/895,533, filed on Oct. 25, 2013.

(51) Int. Cl.

| | |
|---|---|
| ***C12N 15/85*** | (2006.01) |
| ***C12Q 1/37*** | (2006.01) |
| ***C07K 14/435*** | (2006.01) |

(52) U.S. Cl.

CPC .......... *C12Q 1/37* (2013.01); *C07K 14/43595* (2013.01); *C07K 2319/03* (2013.01); *C07K 2319/50* (2013.01); *C07K 2319/60* (2013.01); *G01N 2333/952* (2013.01)

(58) Field of Classification Search

CPC ...................................................... C12N 15/85

See application file for complete search history.

(56) References Cited

U.S. PATENT DOCUMENTS

| | | | |
|---|---|---|---|
| 9,526,345 | B2 | 12/2016 | Tucker |
| 2012/0309039 | A1 | 12/2012 | Atapattu |
| 2012/0322092 | A1 | 12/2012 | Tucker |
| 2013/0065259 | A1 | 3/2013 | Kalcum |

FOREIGN PATENT DOCUMENTS

| | | | | |
|---|---|---|---|---|
| EP | 1131471 | | 10/2002 | |
| EP | 1131471 | B1 * | 10/2002 | ......... C07K 14/4721 |
| WO | 0026408 | | 5/2000 | |
| WO | WO200026408 | * | 5/2000 | ............... C12Q 1/68 |
| WO | 2012166943 | | 12/2012 | |

OTHER PUBLICATIONS

International Search Report dated Feb. 6, 2015, for PCT Application No. PCT/US2014/062260, filed on Oct. 2014.

Arai, Ryoichi; et al. "Design of the Linkers Which Effectively Separate Domains of a Bifunctional Fusion Protein," Protein Engineering, vol. 14, No. 8, 2001. pp. 529-532.

Washbourne, Philip; et al. "Botulinum Neurotoxin Types A and E Require the SNARE Motif in SNAP-25 for Proteolysis," Federation of European Biochemical Societies, 1997, FEBS Letters 418. pp. 1-5.

* cited by examiner

*Primary Examiner* — Tekchand Saidha

(74) *Attorney, Agent, or Firm* — Fish IP Law LLP

(57) ABSTRACT

Compositions and methods are disclosed that provide a rapid, sensitive, and accurate cell-based assay for enzyme activity, particularly for enzyme activities associated with *botulinum* toxins. A cell is provided that expresses a construct that includes an anchor region, a cleavage site, and a reporting region having two or more identical reporter peptides. Enzymatic activity at the cleavage site releases the reporter region into the cytosol, where multiple degradation events occur. The observed change in the signal is proportional to the enzymatic activity.

13 Claims, 21 Drawing Sheets

Specification includes a Sequence Listing.

ENZYME ASSAY WITH DUPLICATE FLUOROPHORES

This application is a divisional of U.S. patent application Ser. No. 14/523,712, filed Oct. 24, 2014, which claims the benefit of U.S. Provisional Application No. 61/895,533 (filed Oct. 25, 2013), U.S. Provisional Application No. 61/897,352 (filed Oct. 30, 2013), U.S. Provisional Application No. 62/014,586 (filed Jun. 19, 2014), and U.S. Provisional Application No. 62/058,532 (filed Oct. 1, 2014).

FIELD OF THE INVENTION

The field of the invention is protease assays, especially those related to *Clostridium botulinum* neurotoxins.

BACKGROUND

*Botulinum* neurotoxins (BoNTs) are produced by *Clostridium botulinum,* and are among the most potent toxins known. These toxins are a well-recognized source of food poisoning, often resulting in serious harm or even death of the victims. There are a number of structurally similar *botulinum* neurotoxins or serotypes (BoNT/A-G, and a proposed BoNT/H), each of which is composed of a heavy chain (~100 kD) and a light chain (~50 kD). The heavy chain mediates toxin entry into a target cell through receptor-mediated endocytosis. Once internalized, the light chain is translocated from the endosomal vesicle lumen into the cytosol, and acts as a zinc-dependent protease to cleave substrate specific proteins that mediate vesicle-target membrane fusion, a process that is central to neurotransmitter release.

BoNT substrate proteins include the cell membrane protein syntaxin, peripheral membrane protein SNAP-25, and the vesicular membrane protein synaptobrevin (Syb). These proteins are collectively referred to as SNARE (soluble N-ethylmaleimide-sensitive factor attachment protein receptor) proteins. Cleavage of SNARE proteins blocks vesicle fusion with the cell membrane and abolishes neurotransmitter release at neuromuscular junctions. Among the SNARE proteins, syntaxin and SNAP-25 usually reside on the target membrane and are thus referred to as t-SNAREs, while synaptobrevin is associated exclusively with synaptic vesicles within the synapse and is referred to as a v-SNARE. Together, these three proteins form a complex that is thought to be the minimal machinery needed to mediate fusion between vesicle membrane and plasma membrane. BoNT/A, E, and C cleave SNAP-25, whereas BoNT/B, D, F, and G cleave synaptobrevin (Syb) at separate and distinct sites. BoNT/C also cleaves syntaxin in addition to SNAP-25. Since BoNTs act as enzymes, even minute quantities can have a devastating effect on an affected individual.

While *botulinum* toxin is a source of food poisoning and has the potential for use as a bioterrorism weapon, there are therapeutic applications. Recently, *botulinum* toxin has been utilized to treat conditions associated with unwanted muscle contractions (such as strabismus) and in the treatment of persistent migraines. It is also widely used for cosmetic purposes, where the selective paralysis of small muscles beneath the skin temporarily reduces the appearance of age-related wrinkles. With such widespread use there is a need to sensitively and speedily characterize BoNT proteins. This process is complicated by the need to accurately quantify BoNT activity rather than simply quantify the amount of BoNT protein present, as purification processes utilized in isolating these proteins can lead to a significant degree of denaturation and resulting inactivation of these proteins.

Currently, a commonly used method to detect BoNTs and quantify their activity is to perform toxicity assays using mice. Such methods require the use of large numbers of mice, are time-consuming, and cannot be used to study toxin catalytic kinetics. A number of immunoassay systems based on antibodies developed against BoNT proteins have also been developed, but while such assays may be useful for quantifying the amount of BoNT protein present they cannot be used to determine the toxin's enzymatic activity. Methods have been developed to detect BoNT reaction products in order to measure enzymatic activities of these toxins, for example, using HPLC or immunoassays directed to cleavage products. These methods, however, are generally complex, time-consuming, and can be expensive (for example, utilizing specialized antibodies), making them difficult to automate and inapplicable for large-scale screening.

Recently, researchers have begun exploring the use of fluorescence resonance energy transfer (FRET) methods for quantifying enzymatic activities. FRET methods involve the use of two fluorescent moieties, a donor fluorophore and an acceptor fluorophore. The emission spectrum of the donor fluor overlaps the excitation spectrum of the acceptor fluor, and under defined conditions and at proper fluorophore spacing and orientation excitation of the donor fluor can lead to emission from the acceptor fluor. The efficiency of this energy transfer is highly dependent upon the distance between the donor fluor and the acceptor fluor, and numerous fluorescence assays have been developed to exploit this phenomenon. For application in cell-based assays, such FRET probes can be generated within the cell by genetic manipulation. In such an approach fluorescent proteins, in particular Green Fluorescent Protein and variants thereof as described in International Patent Application WO2008/145301A1 (to Tasdemir and Corazza), are often used as these proteins do not require the addition of a cofactor or substrate in order to fluoresce. Some of these assays are capable of detecting enzymatic activity. For example, U.S. Pat. No. 7,749,759 (to Fernandez-Salas, Steward, and Aoki) discloses the use of cells containing a substrate for a *Clostridium* toxin, where the substrate (which is expressed from a genetic construct) includes a donor fluorophore and an acceptor fluorophore separated by a peptide that is cleaved by the *Clostridium* toxin. Exposure to the *Clostridium* toxin results in cleavage of the substrate, and the subsequent separation between the donor fluorophore and the acceptor fluorophore results in changes in the observed fluorescence. Such FRET-based assays, however, have limitations. The excitation spectra of the donor fluorophore and of the acceptor fluorophore frequently overlap, resulting in an inherently high background signal from the acceptor fluorophore even in the absence of FRET. Similarly, in some reporter constructs the fluorophores may self aggregate, forming fluorophore complexes within and/or between aggregated constructs that do not dissociate on cleavage of a target site. In addition, the use of longer peptide sequences as cleavage sites in order to accommodate more complex enzyme binding and cleavage sites (for example, those of *Clostridial* neurotoxins) can dramatically reduce the efficiency of energy transfer between fluorophores separated by such peptide sequences.

As a result of this low efficiency and high background fluorescence, FRET-based constructs are often overexpressed within cells, resulting in undesirable cell toxicity and construct aggregation. U.S. Pat. No. 6,936,428 (to Davis and Vellencourt) describes an approach in which background fluorescence in FRET constructs that utilize donor and acceptor fluorescent proteins is reduced by using constructs in which pairs of multimeric protein fluorophores are positioned to form intramolecular homodimers, thereby reducing the formation of donor/acceptor heterodimers that generate background fluorescence. Alternatively, U.S. Pat. No. 8,067,231 (to Fernandez-Salas et al) describes a cell-based assay in which a change in the distribution of observable fluorescence from a cell membrane to the cell cytoplasmic space is observed, however such characterization requires sophisticated optical instruments and image analysis.

All other publications referenced herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, improved compositions and methods are therefore needed to provide rapid and accurate characterization of BoNTs and BoNT activities.

SUMMARY OF THE INVENTION

The present invention provides compositions and methods for use in assays that detect *botulinum* neurotoxins (BoNTs) which utilize a construct that includes at least two instances of the same reporter, such as a fluorophore or chromophore. The construct includes an anchoring site that attaches the construct to a cell and/or vesicle membrane, which in turn provides protection of the reporter from a degradative activity in the cytosol. The construct also includes a cleavage site that separates the anchoring site from at least one of the reporters and also serves as a substrate for an enzyme activity (for example, protease activity). Enzyme activity at the cleavage site releases reporter from the construct; subsequent degradation of the reporters in the cytosol results in a measureable change from a baseline signal that is proportional to enzyme activity.

Embodiments of the inventive concept include a reporting construct that can be used for characterizing an enzyme activity (for example, the activity of a *botulinum* neurotoxin), and cells that include a nucleic acid encoding for such a reporting construct. The reporting construct includes a membrane anchoring domain that interacts with a membrane of a cell (for example, a plasma membrane or a vesicle membrane), a reporter domain that includes two or more occurrences of a signal generating peptide (for example, a peptide sequence corresponding to a fluorescent protein or having at least 80% sequence identity to Green Fluorescent Protein), and a cleavage site that is located between the membrane anchoring site and the reporter domain. The signal generating peptides produce indistinguishable signals, and the total signal produced by the reporter domain is an aggregate of these individual yet indistinguishable signals. The cleavage site includes a peptide that is susceptible to cleavage by the enzyme activity (for example a SNARE protein or a fragment thereof), and such cleavage results in the release of the reporter domain into the cytoplasm. Such cleavage sites can be selected to be susceptible to cleavage by more than one enzyme (for example, both BoNT/A and BoNT/E). The reporter domain undergoes degradative events following release into the cytoplasm, with separate degradative events causing a loss of signal from each of the signal generating peptides and resulting in a gradual loss of the aggregate signal of the reporter domain. In some embodiments a linker peptide is interposed between the signal generating peptides. In a preferred embodiment of the inventive concept, the construct can be cleaved by more than one enzyme, and shows reduced bias in regards to susceptibility of cleavage by one enzyme activity (for example BoNT/A) over a second enzyme activity (for example BoNT/E) relative to an analogous construct having a reporting domain with a single signal generating peptide. In some embodiments the reporting construct includes an auxiliary reporting domain that provides a signal that is distinguishable from that of the reporter domain.

Another embodiment of the inventive concept is a method for characterizing an enzyme activity by providing a cell that expresses a reporting construct, contacting the cell with a sample suspected of including the enzyme activity, and observing a decrease in a signal generated by the reporting construct in the presence of the enzyme activity. The reporting construct includes a membrane anchoring domain that interacts with a membrane of a cell (for example, a plasma membrane or a vesicle membrane), a reporter domain that includes two or more occurrences of a signal generating peptide (for example, a peptide sequence corresponding to a fluorescent protein and/or having at least 80% sequence identity to Green Fluorescent Protein), and a cleavage site that is located between the membrane anchoring site and the reporter domain. The signal generating peptides produce indistinguishable signals, such that the total signal produced by the reporter domain is an aggregate of these individual yet indistinguishable signals. The cleavage site includes a peptide that is susceptible to cleavage by the enzyme activity (for example a SNARE protein or a fragment thereof), and such cleavage results in the release of the reporter domain into the cytoplasm. The reporter domain undergoes degradative events following release into the cytoplasm, with separate degradative events causing a loss of signal from each of the signal generating peptides and resulting in a gradual loss of the aggregate signal of the reporter domain. In some embodiments the aggregate signal of the reporter domain is observable following the loss of the signal from one of the signal generating peptides from a degradative event. In a preferred embodiment of the inventive concept, the construct can be cleaved by more than one enzyme, and shows reduced bias in regards to susceptibility of cleavage by one enzyme activity (for example BoNT/A) over a second enzyme activity (for example BoNT/E) relative to an analogous construct having a reporting domain with a single signal generating peptide.

In some methods of the inventive concept a reference signal is provided that is distinguishable from the signal provided by the reporter domain and can be utilized for normalization of the signal from the reporter domain of the reporting construct. In some embodiments the reference signal is provided by including an auxiliary reporter with the construct, where the auxiliary reporter produces a signal distinguishable from the reporter domain and is not affected by the enzyme activity In other embodiments the reference signal is provided by contacting the cell with a cell dye (for example a membrane dye or a nucleus/nuclear dye). Such a cell dye can be brought into contact with the cell before, during, or after contacting the cell with the enzyme activity.

BRIEF DESCRIPTION OF THE DRAWINGS

FIGS. 1A to 1C schematically depict constructs of the inventive concept that have two identical reporting peptides in various configurations. FIG. 1D shows typical results for a cell-based assay for two different *botulinum* neurotoxins (BoNT/A, BoNT/E), utilizing a reporter configured as shown in FIG. 1A. Results are also shown for cells expressing an analogous construct carrying a single reporter. Surprisingly, the bias between BoNT/A and BoNT/E sensitivity is dramatically reduced in cells expressing the construct of the inventive concept.

DETAILED DESCRIPTION

Figure 1A:
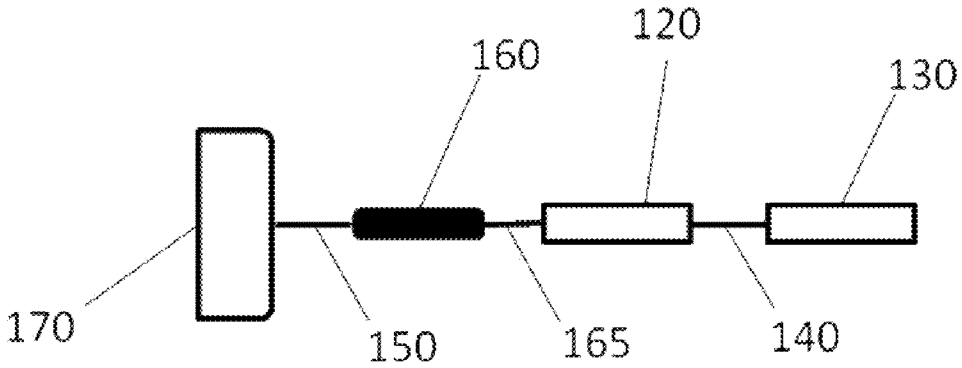
FIGS. 1A to 1D schematically depict constructs of the inventive concept and show typical results.

Embodiments of the inventive concept utilize one or more cells that include a construct (for example introduced via expression following transfection and/or microinjection) that includes components that sequester an observable reporter moiety or region in a protected region and an analyte-sensitive region. The reporter moiety can include two or more identical reporters. Such protected regions can be in proximity to a cell membrane and/or a vesicle membrane. Interaction of the analyte sensitive region with the analyte results in the release of the reporter from the protected region by a cleavage event, which results in the degradation of the reporter and an observable change in the signal from the reporter. Examples of analytes can include proteolytic enzymes, and in such cases the analyte sensitive region can be a cleavage site that can serve as an enzyme substrate.

Various objects, features, aspects and advantages of the inventive subject matter will become more apparent from the following detailed description of preferred embodiments, along with the accompanying drawing figures in which like numerals represent like components.

Embodiments of the inventive concept include methods in which such constructs are expressed in cells, which are subsequently exposed to an analyte of interest (for example, a *Clostridium botulinum* and/or *Clostridium tetani* toxin). Such cells can be division arrested cells. It should be appreciated that the novel arrangement and composition of constructs of the inventive concept has a direct impact on the mechanism and performance characteristics of such assays.

In preferred embodiments of the inventive concept exposure to the analyte of interest results in a cleavage event at an analyte sensitive region or domain of the construct, resulting in the release of a construct fragment that includes a reporter region carrying two or more identical signal generating regions (for example a pair of identical fluorophores) each of which generate a detectable signal. Unlike constructs and methods utilizing fluorophores arranged as FRET pairs (for example, different fluorophores arranged as hetero-FRET pairs and/or similar or identical fluorophores arranged as homo-FRET pairs), each of the signal generating regions of a reporter released as a construct fragment contributes directly to a detectable aggregate signal both before and immediately following the cleavage event. For example, in some embodiments such an aggregate signal can be an approximate summation (or other function) of the signal observed from each of the signal generating regions. In constructs and assays of the inventive concept the change in the detectable signal that forms the basis of detection is a result of multiple degradation events that occur in the cytosol subsequent to the cleavage event, as loss of one of a pair of identical signal generating regions (for example, a pair of essentially identical fluorophores) still providing an emitting reporter fragment. In a construct utilizing a single reporter, a single degradation event occurring at a released construct fragment can result in fragmentation of the single reporter and loss of the detectable signal. Similarly, in constructs utilizing duplicate reporters in which the detectable signal is a result of interaction between the reporters (for example, a construct utilizing a pair of fluorophores arranged to perform hetero-FRET and/or homo-FRET) the fragmentation of a single signal generating region due to a single degradation event also results in a loss of the detectable signal from that construct.

In contrast, a reporter-containing fragment generated by a cleavage event directed to a construct of the inventive concept that is configured to release two or more identical/indistinguishable signal generating regions following the cleavage event can continue to provide a detectable signal following a single degradation event occurring at one of the occurrences of the signal generating region. Since multiple degradation events are required to halt the generation of detectable signal by the construct cleavage fragment, the detectable signal decreases with increasing analyte concentration but persists (relative to single reporter constructs or constructs that depend upon paired reporters for signal generation) at high analyte concentrations. This can result in an improved dynamic range for assays based on constructs of the inventive concept.

The components of a construct of the inventive concept can be arranged in a variety of ways. The following description includes a number of examples in which functional domains of a reporting construct, for example, a membrane anchor (A), a cleavage site (B), multiple occurrences of a primary signal generating region/reporter (C, C'), and in some instances a secondary reporter (D) are depicted as being joined in various arrangements by linker regions or linkers (-). It should be appreciated that, in the following figures and their descriptions, the presence of these linkers can be considered optional. As such, in embodiments of the inventive concept one or more portions described as a linker can be omitted. In some embodiments linker regions of the inventive concept can also include portions of a functional region that are not directly involved in the function of that region. For example, if a reporter is a protein fluorophore a linker can be a portion of the protein fluorophore sequence that is not directly involved in fluorescence. Similarly, a linker can be a portion of cleavage site sequence that does not directly serve as a protease substrate. Alternatively, in other embodiments of the inventive concept a linker can be a synthetic or engineered peptide sequence, which can, for example, be designed to reduce FRET (i.e. homo-FRET and/or hetero-FRET) between signal generating regions to non-useful levels (for example, less than about 5%). Such a synthetic peptide sequence can be a flexible sequence, a rigid sequence, or a sequence with both flexible and rigid portions. SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, and SEQ ID NO. 9 show exemplary synthetic linker sequences. In some embodiments a linker region can include repeated occurrences of such linker sequences (for example, in a concatemer-like arrangement) to provide desired length, flexibility, and/or other desirable structural features. It should be appreciated that, as used herein, the term "linker" does not denote a cleavage site that is cleaved by an enzyme analyte, but rather a structural region that joins other functional regions of a reporting construct.

In some embodiments the reporter-containing region can contain at least two instances of a primary reporter that is a fluorophore and/or a chromophore. In some embodiments of the inventive concept, two instances of a primary reporter have the same amino acid sequence. In other embodiments, two instances of a primary reporter can have different compositions but have substantially similar (i.e. exhibiting greater than or equal to 80% overlap) excitation and emission spectra. In preferred embodiments a primary reporter can be a fluorescent protein, for example Green Fluorescent Protein (SEQ ID NO. 10) or a peptide having at least 80% sequence identity to the sequence of Green Fluorescent Protein. Suitable fluorescent protein fluorophores include Yellow Fluorescent Protein (for example eYFP, SEQ ID NO. 11), Red Fluorescent Protein, Cyan Fluorescent Protein (SEQ ID NO. 12), mBanana, mStrawberry, mCherry, tdTomato, J-Red, DsRed monomer, mCitrine, Venus (SEQ ID NO. 13), YPet protein, Emerald, EGFP, CyPet, mCFPm, Cerulean, mPlum, mOrange, mKO, T-Sapphire, a derivative of Yellow Fluorescent Protein, a derivative of mCitrine, a derivative of Venus, a derivative of YPet protein, and/or a Green Fluorescent Protein variant. In an especially preferred embodiment, a primary reporter can be a monomeric fluorescent protein derived from the Green Fluorescent Protein of *Aequorea victoria,* such as Sirius, Azurite, EBFP2, TagBFP, mTurqoise, ECFP, Cerulean, TagCFP, mTFP1, mUkG1, mAG1, AcGFP1, TagGFP2, EDFP, mWasabi, EmGFP, TagYFP, eYFP (SEQ ID NO. 11), Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, and/or mKeima (see "Fluorescent Proteins and Their Applications in Imaging Living Cells and Tissues" (Chudakov, D. M. et al, Physiol. Rev. 90:1103-1163, 2010). Similarly, suitable primary reporters can be protein fluorophores derived from the Green Fluorescent Protein of *Aequorea victoria* that include an A206K mutation. Alternatively, a primary reporter can be a non-fluorophore and/or a non-chromophore, for example a fluorescence quencher.

Within constructs of the inventive concept the arrangement of primary reporters within the reporter containing portion can be such that they are sufficiently distant from one another and/or oriented such that they exhibit essentially no useful (i.e. less than 5%) FRET (for example, homo-FRET) energy transfer. Contemplated low levels of homo-FRET energy transfer can be less than or equal to about 1%, less than or equal to about 0.1%, less than or equal to about 0.01%, and/or less than or equal to about 0.001% energy transfer between fluors. Similarly, contemplated low levels of homo-FRET energy transfer can be less than or equal to about 10%, less than or equal to about 1%, less than or equal to about 0.1%, less than or equal to about 0.01%, and/or less than or equal to about 0.001% of the background noise of the observable signal. Alternatively, in some embodiments of the inventive construct the primary reporters 120, 130 can be arranged such that they exhibit significant (i.e. greater than about 1%) homo-FRET energy transfer. Such phenomena can be controlled using the length of a linker region or linker interposed between such primary reporters. In some embodiments of the inventive concept such a linker can have a length of 20, 30, 40 50, or more amino acids. Similarly, the such a linker can have a linear dimension of at least about 4, about 6, about 8, about 10, about 15, about 20 or more nanometers when the construct is in its native, folded state.

It is contemplated that a primary reporter of a construct of the inventive concept can include more than one fluorescent moiety. For example, a pair of fluorophores with different but overlapping excitation and emission spectra could be arranged as a FRET pair that acts as a single instance of a primary reporter. Similarly, a pair of identical fluorophores could be arranged as a homo-FRET pair that acts as a single instance of a primary reporter (for instance, as detected by fluorescence anisotropy). For example, in such an embodiment a reporting construct could include a pair of primary fluorophores, where each primary fluorophore includes two fluorophores with different but overlapping excitation and emission spectra arranged as a hetero-FRET pair. Alternatively, in such an embodiment a reporting construct could include a pair of primary fluorophores, where each primary fluorophore includes two fluorophores with similar or identical excitation and emission spectra arranged as a homo-FRET pair.

As noted above, the domains of a construct of the inventive concept can be arranged in a variety of ways. A preferred embodiment of the inventive concept, which can be characterized as an A-B-C-C' arrangement, is shown schematically in FIG. 1A. Such a reporter construct can include a membrane anchor 170 that is linked to a cleavage site 160 by an interposing anchor/cleavage site linker 150. The cleavage site is in turn linked to a first instance of a pair of identical primary reporters 120 by a cleavage site/reporter linker 165. This first instance of a pair of identical primary reporters 120 is linked to a second instance of a pair of identical primary reporters 130 by an interposing primary reporter/primary reporter linker 140. In such an embodiment the reporter-containing region can contain at least two instances of a primary reporter. An example of a reporter construct having such a structure is shown in SEQ ID NO 14.

Figure 1B:
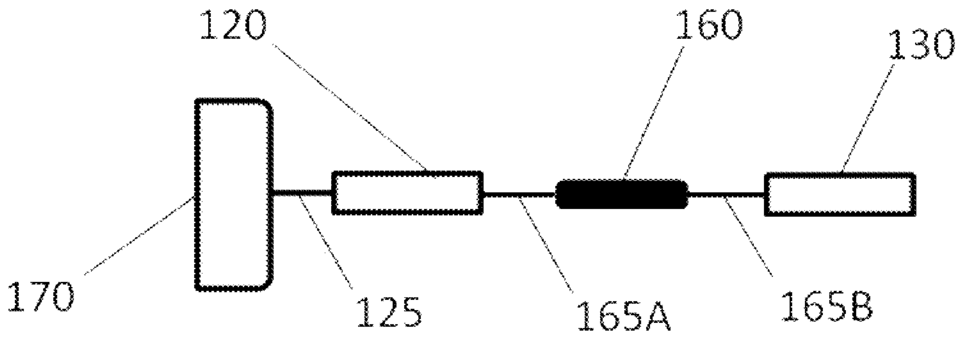

An alternative arrangement of the reporter construct (which can be characterized as A-C-B-C') is shown schematically in FIG. 1B, in which a membrane anchor 170 is linked to a first instance of a pair of identical primary reporters 120 by an interposing anchor/primary reporter linker 125. The first instance of a pair of identical primary reporters 120 is linked to a cleavage site 160 via a first cleavage site/fluor linker 165A. The cleavage site 160 is also linked to a second instance of a pair of identical primary reporters 130 via a second cleavage site/fluor linker 165B. Emission from such a retained reporter 120 can, for example, be used as a baseline or normalizing signal.

Another alternative arrangement of the reporter construct (which can be characterized as C-A-B-C') is shown in FIG.

1C, in which a first instance of a pair of identical primary reporters 120 is linked to a membrane anchor portion 170 by an intervening anchor/primary reporter linker 125. The membrane anchor 170 is also linked to a cleavage site 160 by an anchor/cleavage site linker 150. The cleavage site is 160 is, in turn, linked to a second instance of a pair of identical primary reporters 130 via a cleavage site/reporter linker 165. Emission from such a retained reporter 120 can, for example, be used as a baseline or normalizing signal. Although one representation of this configuration is shown, it should be appreciated that the reporter linker 140 can be placed on either side of the cleavage site 160 in such an embodiment.

Figure 1C:
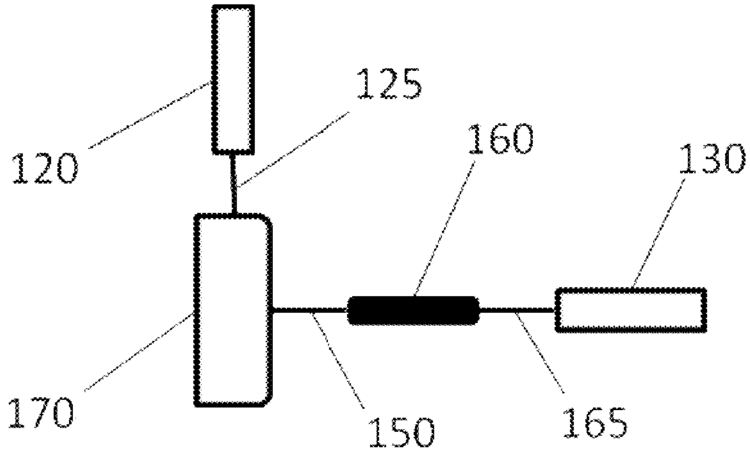

In the configurations for the construct shown in FIG. 1A, FIG. 1B, and FIG. 1C hydrolysis of the cleavage site 160, for example by a protease, results in the release of one or more primary reporters 120, 130 from the membrane anchoring domain 170. The cleavage site, therefore, at least partially determines the specificity of assays based upon such constructs for specific enzyme activities, and preferably includes hydrolysis sites where enzyme activity results in cleavage of the peptide backbone of the construct and recognition sites that provide interaction sites with the enzyme and confer at least a portion of substrate specificity. In some embodiments the cleavage site can include regions that interact with exosites or allosteric sites of a target enzyme. In preferred embodiments of the inventive concept the cleavage site is susceptible to cleavage by a botulinum neurotoxin BoNT protease activity, for example BoNT/A, BoNT/B, BoNT/C, BoNT/D, BoNT/E, BoNT/F, and/or BoNT/G. It is contemplated that a cleavage site sequence can be selected or designed to provide cleavage and recognition sites for two or more different BoNTs (for example, both BoNT/A and BoNT/E). In some embodiments the cleavage site can include intact sequences or sequences derived from a SNARE protein, such as a synaptosomal-associated protein (for example, SNAP-25; SEQ ID NO. 10), a vesicle associated membrane protein (for example, VAMP or synaptobrevin; SEQ ID NO. 11), and/or sequences derived from a syntaxin. Examples of suitable cleavage site sequences include SEQ ID NO. 15, SEQ ID NO. 16, SEQ ID NO. 17, and SEQ ID NO. 18.

As noted above, release from a membrane anchoring domain can permit one or more primary reporters to diffuse away from a protected region. Such protected regions can include proximity to a cell membrane and/or to a vesicle membrane. Towards that end an anchoring domain can include a cell membrane localizing peptide and/or a vesicle membrane localizing peptide. Such an anchoring region can include a transmembrane region in which at least a portion of the peptide chain enters and/or passes through a membrane of the cell. Alternatively, an anchoring region can include a palmitoylation site that, following post-translational processing by the cell, provides a site that interacts with a membrane of the cell. Alternatively, a membrane anchoring site can include a peptide sequence that interacts with a membrane-bound receptor or ligand. In some embodiments of the inventive concept an anchoring domain can include sequences derived from a synaptobrevin (for example a transmembrane peptide of synaptobrevin) and/or from SNAP-25 (for example a palmitoylation region of SNAP-25). In other embodiments of the inventive concept a membrane anchoring domain can be a syntaxin or a syntaxin fragment.

As noted above, once released from an anchoring region 170, primary reporters can diffuse into the cytosol. Use of two or more primary reporters provides a number of technical advantages. Advantages of constructs that release two or more primary reporters upon cleavage are described above. Other advantages include the ability to utilize lower expression levels for the construct (thereby minimizing the risk of toxicity and/or construct aggregation) and/or the ability to utilize far fewer cells in a cell-based assay. In addition, the relatively strong signal generated by multiple primary reporters can provide for more stable and reproducible baseline measurements, which also serve to increase assay sensitivity by permitting more robust differentiation of signal from noise. It should be noted that previous investigators (A. G. von Armin, X. W. Deng, and M. G. Stacey; Gene 221 (1998), pp. 35-43) have utilized constructs incorporating two or more sets of Yellow Fluorescent Protein sequences as markers for gene expression but found bright fluorescence throughout the cells, such constructs failing to demonstrate the degradative events that are not only characteristic of constructs of the inventive concept but that are necessary for their utilization in cell-based assays.

Figure 1D:
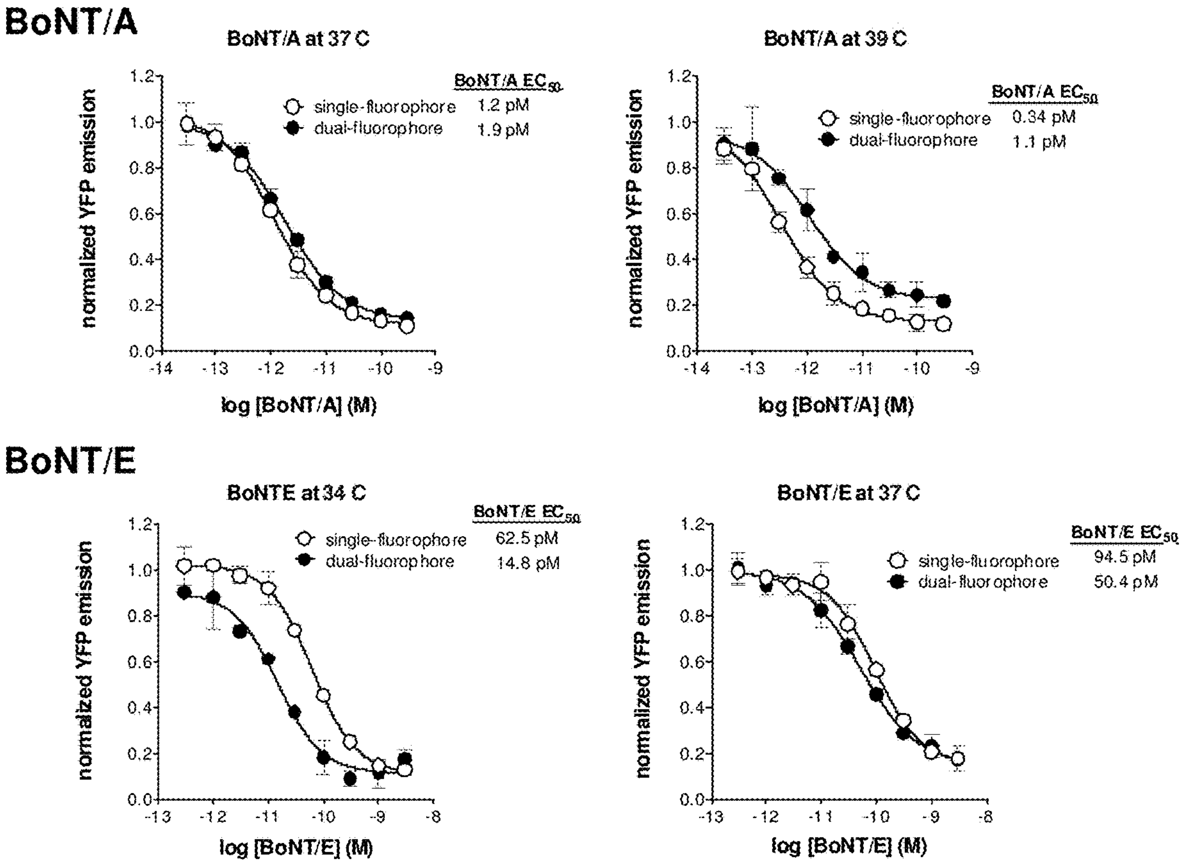

Surprisingly, the inventors have found that constructs with reporting regions that include multiple primary reporters can provide different selectivity between enzyme targets compared to analogous constructs in which the reporting region contains a single occurrence of a primary reporter. An example of this is found in FIG. 1D, which shows comparative data for the response of cell based assays to BoNT/A and to BoNT/E, where the cells include either a construct of the inventive concept that includes two eYFP protein fluorophores in an A-B-C-C' arrangement or an analogous construct that includes a single eYFP protein fluorophore in an A-B-C arrangement. Both BoNT/A and BoNT/E recognize and cleave the cleavage site of both constructs, however the single fluorophore construct has an approximately 80-fold bias (i.e. approximately 80-fold better sensitivity, as expressed in terms of $EC_{50}$) for the BoNT/A neurotoxin over the BoNT/E neurotoxin (see FIG. 1D, 37° C.). The same study performed using cells expressing the "dual fluorophore" reporting construct (i.e. the construct carrying two eYFP fluorophores) showed similar sensitivity to BoNT/A but increased sensitivity to BoNT/E, reducing the assay bias to 26-fold. This reduction in assay bias advantageously permits the same construct to be used for assays directed towards more than one enzyme analyte. Without wishing to be bound by theory, the inventors believe that the use of additional fluorescent peptide sequences imparts a tertiary structure to the construct that provides improved access to a greater number of recognition sites within the cleavage domain of the construct.

In some embodiments of the inventive concept a reporter construct can include, in addition to two or more primary reporters, a secondary reporter that differs from the primary reporters. The secondary reporter can have a distinct or different chemical structure from that of the primary reporters. Such a secondary reporter can have an emission spectrum that overlaps the excitation spectrum of a primary reporter. In such an embodiment the construct can be arranged so that significant FRET (i.e. greater than about 1%) occurs between a secondary reporter and a primary reporter. In a preferred embodiment the secondary reporter is a fluorescent protein, such as Yellow Fluorescent Protein, Red Fluorescent Protein, Cyano Fluorescent Protein, Green Fluorescent Protein, mBanana, mStrawberry, mCherry, tdTomato, J-Red, DsRed monomer, mCitrine, Venus, YPet protein, Emerald, EGFP, CyPet, mCFPm, Cerulean, mPlum, mOrange, mKO, T-Sapphire, a derivative of Yellow Fluorescent Protein, a derivative of mCitrine, a derivative of Venus, a derivative of YPet protein, and/or a Green Fluorescent Protein variant.

Preferably, the reporter construct can be arranges such that significant or useful FRET does not occur (i.e. the degree of FRET that occurs is less than or equal to 5%) between the secondary reporter and a primary reporter. The arrangement of the secondary reporter and at least one of the primary reporters within the reporter construct can be such that they are sufficiently distant from one another that they exhibit essentially no useful (i.e. less than or equal to 5%) FRET. Contemplated non-useful levels of FRET energy transfer can be less than or equal to about 10%, less than or equal to about 5%, less than or equal to about 1%, or less than or equal to about 0.1% of the associated background fluorescence. This can be accomplished by selecting a linker that provides sufficient distance between the secondary reporter and a primary reporter. In some embodiments of the inventive concept such a linker can have a length of 20, 25, 30, 35, 40, 45, 50, 55, 60, 65 or more amino acids. Similarly, the a linker between two primary reporters can have a length of at least about 4, about 6, about 8, about 10, about 15, about 20 or more nanometers when the construct is in its native, folded state. Suitable linkers can include synthetic peptides, and such peptides can be flexible peptides, rigid peptides, or can include both flexible and rigid portions.

In some embodiments of the inventive concept a signal or emission from a secondary reporter can be utilized as a reference or as normalization data useful for adjusting or normalizing a signal observed from one or more reporters of the reporter-containing portion, thereby improving precision and/or sensitivity of an assay utilizing such a construct. In other embodiments a signal or emission from a secondary reporter can be utilized by an image recognition system to identify the location within an acquired image wherein a reaction of the assay can be taking place, thereby simplifying data acquisition.

Figure 2A:
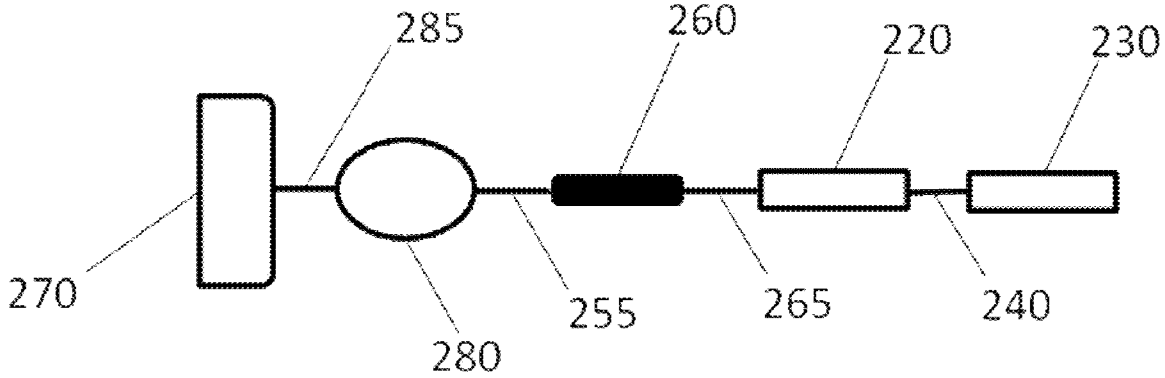
FIGS. 2A to 2K schematically depict constructs of the inventive concept that include two identical reporters and a third, different reporter.

An example of an embodiment that includes such a secondary reporter (which can be characterized as having the structure A-D-B-C-C', where "D" represents the secondary reporter) is shown schematically in FIG. 2A. In such a reporter construct a membrane anchor 270 is linked to a secondary reporter 280 by an intervening anchor/secondary reporter linker 285. The secondary reporter 280 is also linked to a cleavage site 260 by a secondary reporter/cleavage site linker 255. The cleavage site 260 is, in turn, linked to a first instance of a pair of identical primary reporters 220 via a cleavage site/primary reporter linker 265, and the first instance of a pair of identical primary reporters 220 and the second instance of a pair of identical primary reporters 230 are joined by an intervening primary reporter/primary reporter linker 240.

Figure 2B:
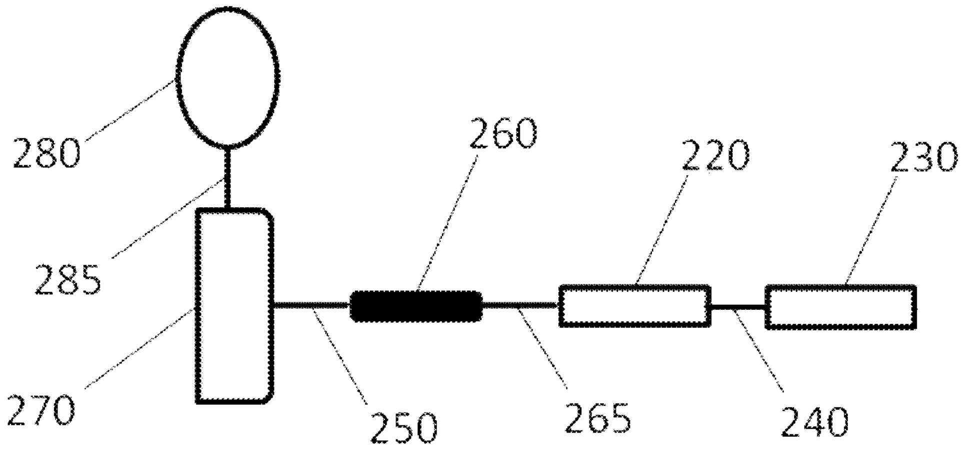

An alternative embodiment of a reporting construct with two or more primary reporters and at least one secondary reporter (which can be described as D-A-B-C-C') is depicted schematically in FIG. 2B. In this embodiment a secondary reporter 280 is coupled to a membrane anchor 270 by an intervening anchor/secondary reporter linker 285. The membrane anchor 270 is in turn linked to a cleavage site 260 by an anchor/cleavage site linker 250. The pair of identical primary reporters 220, 230, which are joined by a primary reporter/primary reporter linker 240 are in turn attached to the cleavage site 260 via a cleavage site/primary reporter linker 265.

Figure 2C:
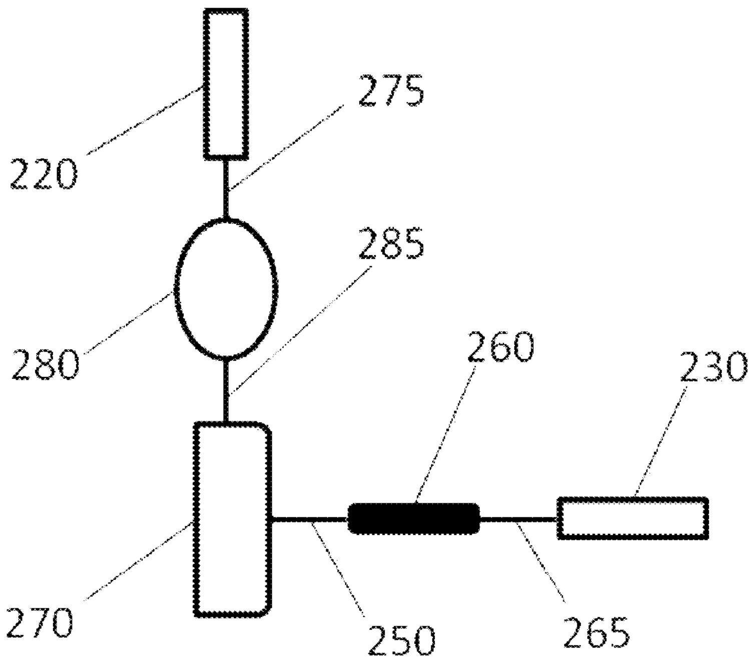

FIG. 2C schematically depicts an embodiment of a reporting construct (which can be described as C-D-A-B-C') in which a first instance of a pair of identical primary reporters 220 is joined to a secondary reporter 280 by a primary reporter/secondary reporter linker 275. The secondary reporter 280 is in turn coupled to a membrane anchor 270 by an intervening anchor/secondary reporter linker 275. The membrane anchor 270 is further joined to a cleavage site 260, with an anchor/cleavage site linker 250 interposed between them. A second instance of a pair of identical primary reporters 230 is also coupled to the cleavage site 260 by a cleavage site/primary reporter linker 265.

Figure 2D:
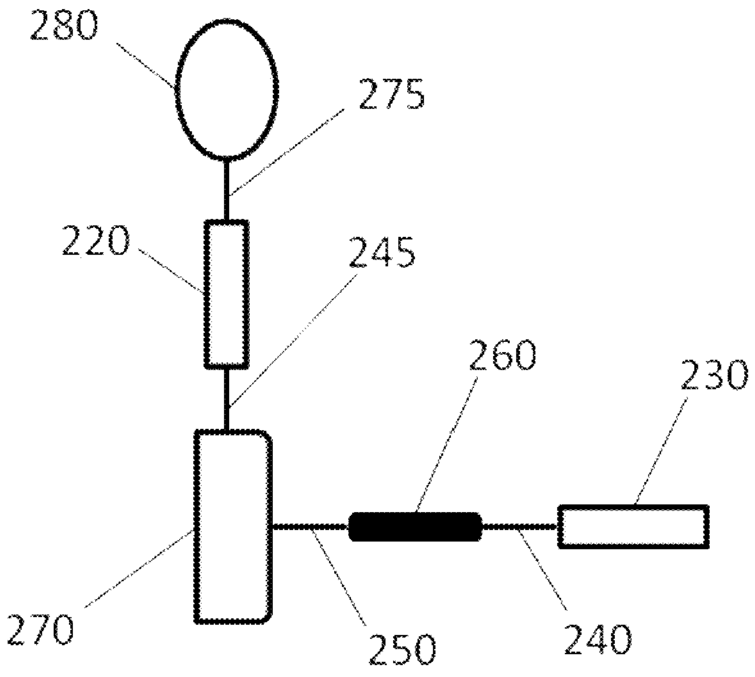

FIG. 2D schematically depicts an embodiment of a reporting construct (which can be described as D-C-A-B-C') in which a secondary reporter 280 is joined to a first instance of a pair of identical primary reporters 220 by a primary reporter/secondary reporter linker 275. The first instance of a pair of identical primary reporters 220 is in turn coupled to membrane anchor 270, with an anchor/primary reporter linker 245 interposed between them. The membrane anchor 270 is also joined to a cleavage site 260 by an anchor/cleavage site linker 250. A second instance of a pair of identical primary reporters 230 is coupled to the cleavage site 260 by an interposing cleavage site/primary reporter linker 240.

Figure 2E:
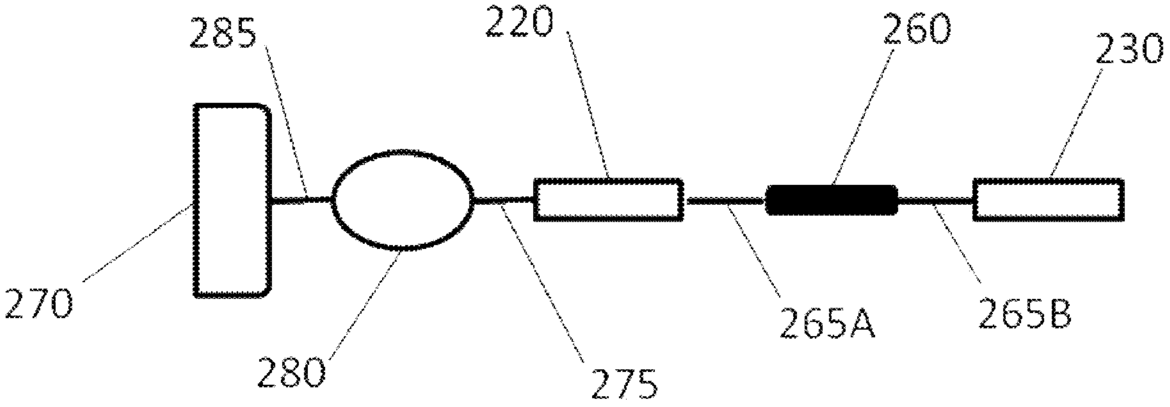

FIG. 2E schematically depicts an embodiment of a reporting construct (which can be described as A-D-C-B-C') in which a membrane anchor 270 is joined to a secondary reporter 280 via an anchor/secondary reporter linker 285. The secondary reporter 280 is also coupled to a first instance of a pair of identical primary reporters 220 by an intervening primary reporter/secondary reporter linker 275. The first instance of a pair of identical primary reporters 220 is in turn coupled to a cleavage site 260 by a cleavage site/primary reporter linker 265A. The second instance of a pair of identical primary reporters 230 is also joined to this cleavage site 260 by another cleavage site/primary reporter linker 265B.

Figure 2F:
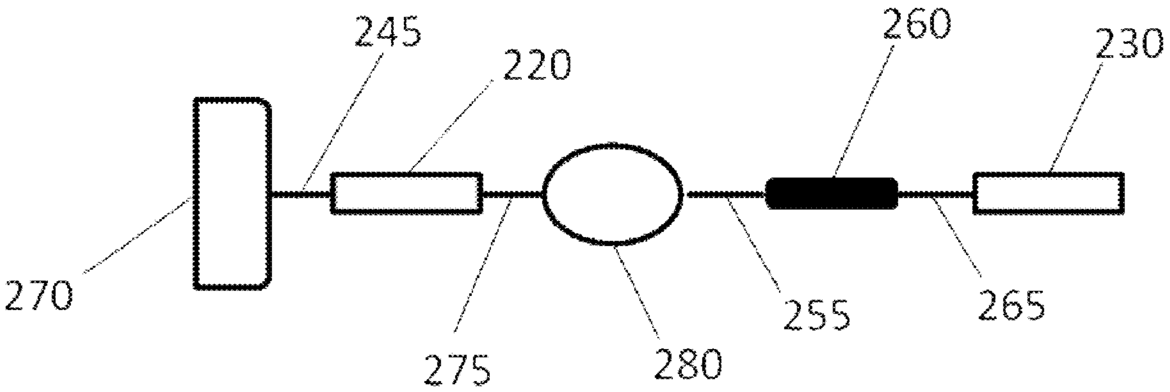

FIG. 2F schematically depicts an embodiment of a reporting construct (which can be described as A-C-D-B-C') in which a membrane anchor 270 is joined to a first instance of a pair of identical primary reporters 220 via an interposing anchor/primary reporter linker 245. A secondary reporter 280 is also coupled to the first instance of a pair of identical primary reporters 220 via a primary reporter/secondary reporter linker 275. This secondary reporter 280 is linked to a cleavage site 260 by a secondary reporter/cleavage site linker 255. Subsequently, the cleavage site 260 is joined to a second instance of a pair of identical primary reporters 230 by a cleavage site/primary reporter linker 265.

Figure 2G:
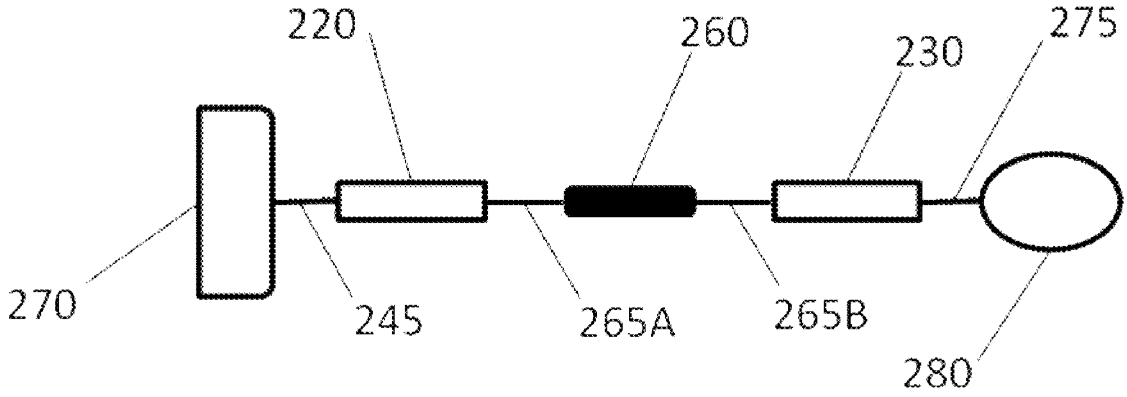

FIG. 2G schematically depicts an embodiment of a reporting construct (which can be described as A-C-B-C'-D) in which a membrane anchor 270 is coupled to a first instance of a pair of identical primary reporters 220 by an anchor/primary reporter linker 245. This first instance of a pair of identical primary reporters 220 is joined to a cleavage site 260 via a first cleavage site/primary reporter linker 265A. The cleavage site 260 is also joined to a second instance of a pair of identical primary reporters 230 by a second cleavage site/primary reporter linker 265B. A secondary reporter 280 is also coupled to the second instance of a pair of identical primary reporters 230 by an intervening primary reporter/secondary reporter linker 275.

Figure 2H:
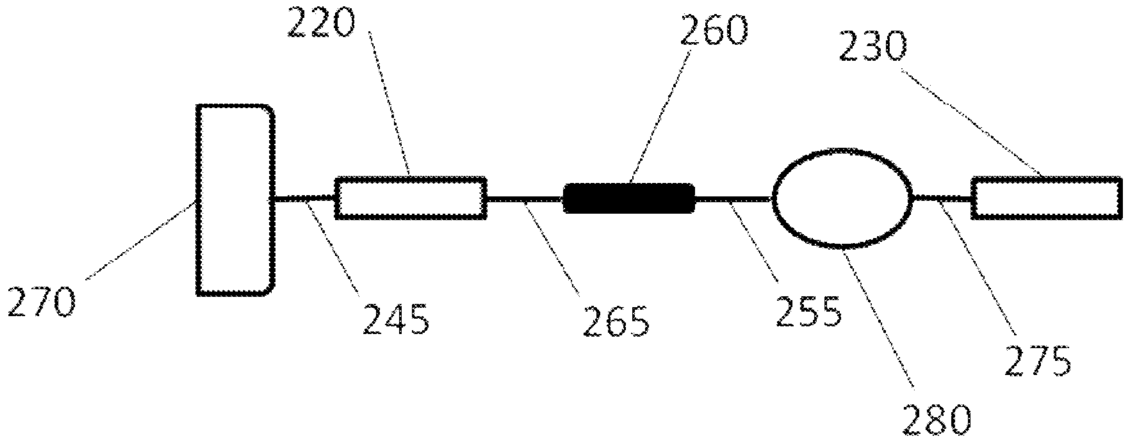

FIG. 2H schematically depicts an embodiment of a reporting construct (which can be described as A-C-B-D-C') in which a membrane anchor 270 is coupled to a first instance of a pair of identical primary reporters 220 by an anchor/primary reporter linker 245. This first instance of a pair of identical primary reporters 220 is joined to a cleavage site 260 via a cleavage site/primary reporter linker 265. The cleavage site 260 is also joined to a secondary reporter 280 by a secondary reporter/cleavage site linker 255. A second instance of a pair of identical primary reporters 230 is also coupled to the secondary reporter 280, by an intervening primary reporter/secondary reporter linker 275.

Figure 2I:
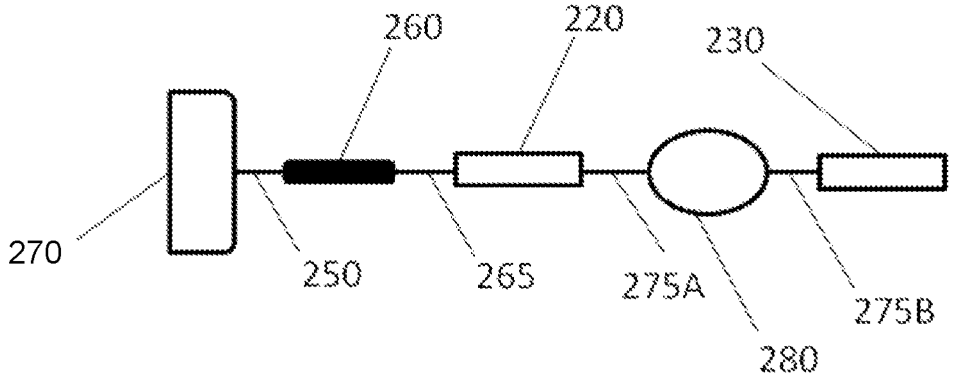

FIG. 2I schematically depicts an embodiment of a reporting construct (which can be described as A-B-C-D-C') in which a membrane anchor 270 is coupled to a cleavage site 260 by an anchor/cleavage site linker 250. This cleavage site 260 is joined to a first instance of a pair of identical primary reporters 220 via a cleavage site/primary reporter linker 265. This first instance of a pair of identical primary reporters 220 is also joined to a secondary reporter 280 by a first primary reporter/secondary reporter linker 275A. A second instance of a pair of identical primary reporters 230 is also joined to the secondary reporter 280 by a second primary reporter/secondary reporter linker 275B.

Figure 2J:
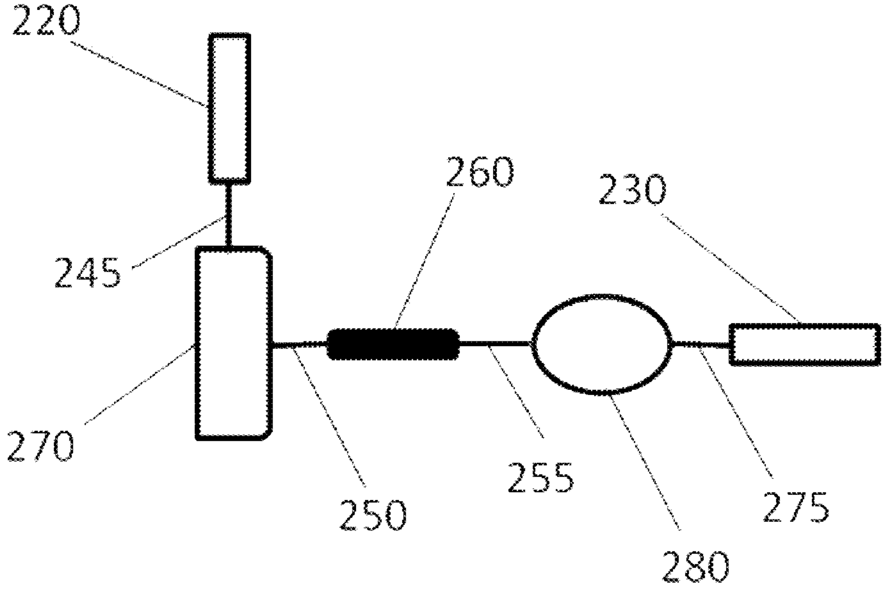

FIG. 2J schematically depicts an embodiment of a reporting construct (which can be described as C-A-B-D-C') in which a first instance of a pair of identical primary reporters 220 is joined to a membrane anchor 270 by an interposing anchor/primary reporter linker 245. The membrane anchor 270 is also coupled to a cleavage site 260 via an anchor/cleavage site linker 250. The cleavage site 260 is subsequently linked to a secondary reporter 280 by a cleavage site/secondary reporter linker 255. A second instance of a pair of identical primary reporters 230 is also linked to the secondary reporter, via a primary reporter/secondary reporter linker 275.

Figure 2K:
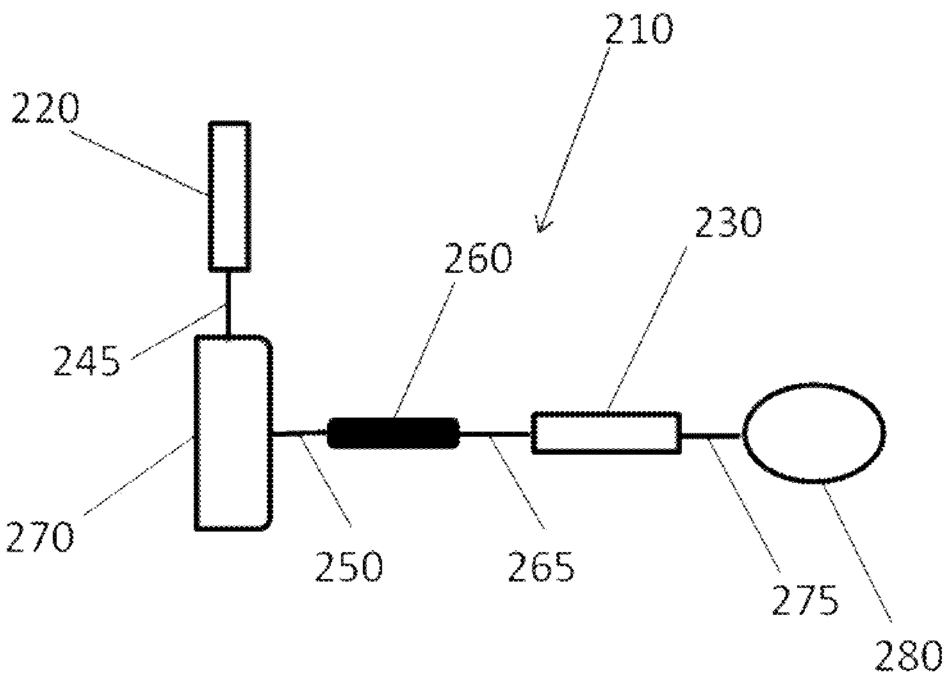

FIG. 2K schematically depicts an embodiment of a reporting construct (which can be described as C-A-B-C'-D) in which a first instance of a pair of identical primary reporters 220 is joined to a membrane anchor 270 by an interposing anchor/primary reporter linker 245. The membrane anchor 270 is also coupled to a cleavage site 260 via an anchor/cleavage site linker 250. The cleavage site 260 is subsequently linked to a second instance of a pair of identical primary reporters 230 by an anchor/primary reporter linker 265. A secondary reporter 280 is also linked to the second instance of a pair of identical primary reporters 230 by a primary reporter/secondary reporter linker 275.

In some embodiments a primary reporter is connected to a secondary reporter by an intervening linker. In some of such embodiments, the primary/secondary linker is selected to provide no significant (i.e. less than 5%) FRET between a primary reporter and a secondary reporter. For example, a primary/secondary reporter linker can be selected to have a length, geometry, and/or rigidity to maintain a distance and/or orientation between a primary reporter and a secondary reporter to reduce FRET to a negligible (i.e. <5%) amount. In other embodiments, a primary/secondary reporter linker can be configured to provide a useful degree of FRET (i.e. >5%) between the primary reporter and a secondary reporter.

Figure 3:
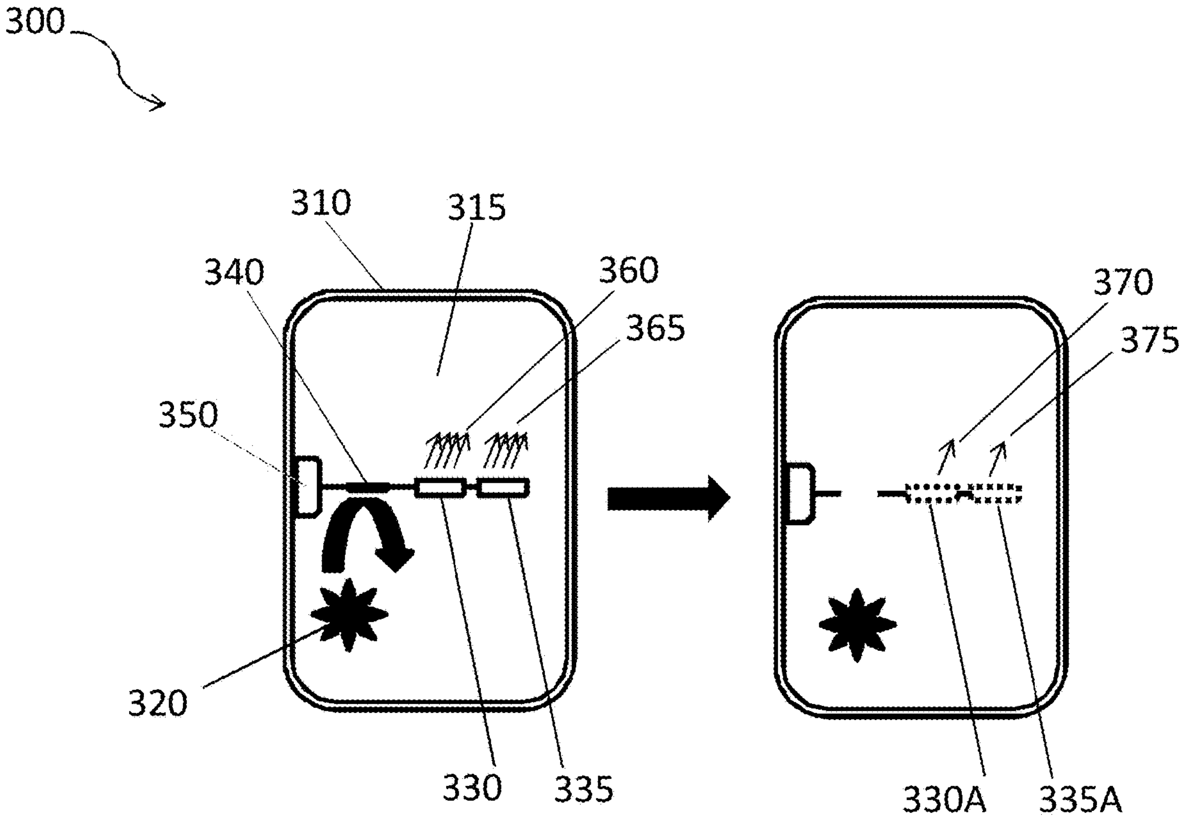
FIG. 3 depicts a cell-based assay of the invention in which the construct includes a cell membrane anchoring domain.

FIG. 3 depicts a schematic of an exemplary assay 300 of the inventive concept. A cell with a cell membrane 310 and cytosol 315 has expressed a construct that includes a cell membrane anchoring portion 350, a cleavage site 340, and two identical reporters 330, 335. Anchored to the cell membrane 310, the reporters 330, 335 produce a strong signal 360, 365. To perform the assay the cell is exposed to an enzyme activity 320, which can act on the cleavage site 340. Hydrolysis of the peptide backbone of the cleavage site releases the reporters into the cytosol 315. Subsequent multiple degradative events result in degraded reporters 330A, 335A that produce a modified signal 370, 375. In some embodiments of the inventive concept the reporters are fluorescent proteins, and the fluorescence signal from the degraded fluorescent proteins is reduced.

Figure 4:
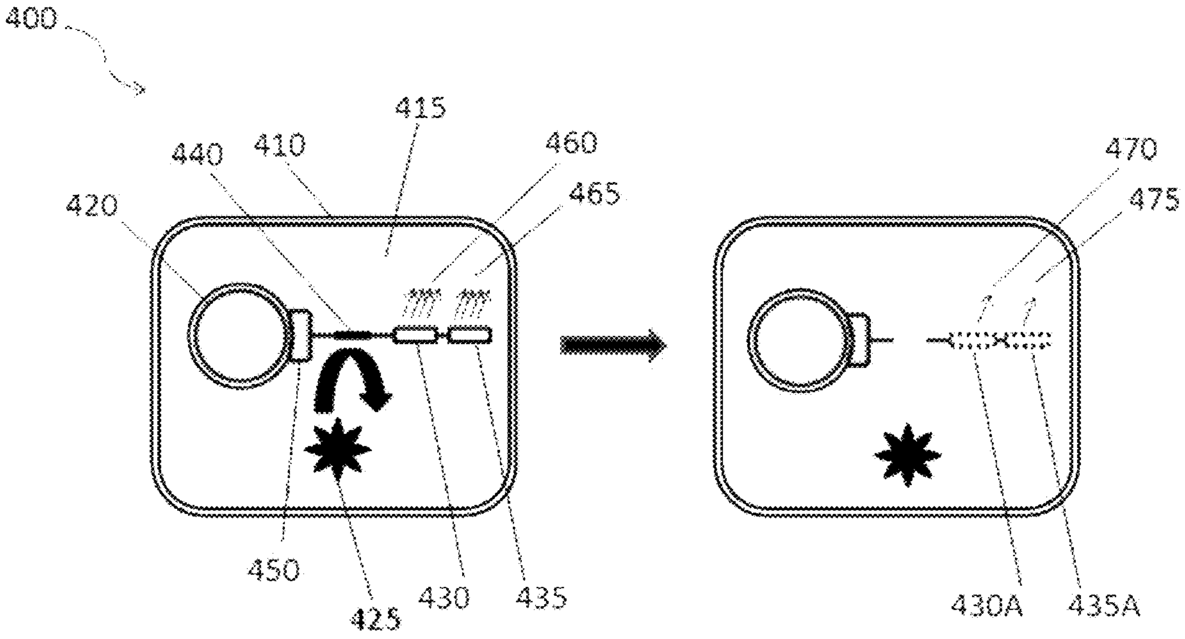
FIG. 4 depicts a cell-based assay of the invention in which the construct includes a vesicle membrane anchoring domain.

FIG. 4 depicts an alternative assay 400 of the inventive concept. A cell with a cell membrane 410, cytosol 415, and a vesicle 420 has expressed a construct that includes a vesicle membrane anchoring portion 450, a cleavage site 440, and two reporters 430, 435. Anchored to the vesicle 420, the reporters 430, 435 produce a strong signal 460, 465. To perform the assay the cell is exposed to an enzyme activity 425, which can act on the cleavage site 440. Hydrolysis of the cleavage site releases the reporters, resulting in release of the reporters 430, 435. Subsequent multiple degradative event results in degraded reporters 430A, 435A that produce a modified signal 470, 475. In some embodiments of the inventive concept the reporters are fluorescent proteins, and the fluorescence signal from the degraded fluorescent proteins is reduced.

Figure 5:
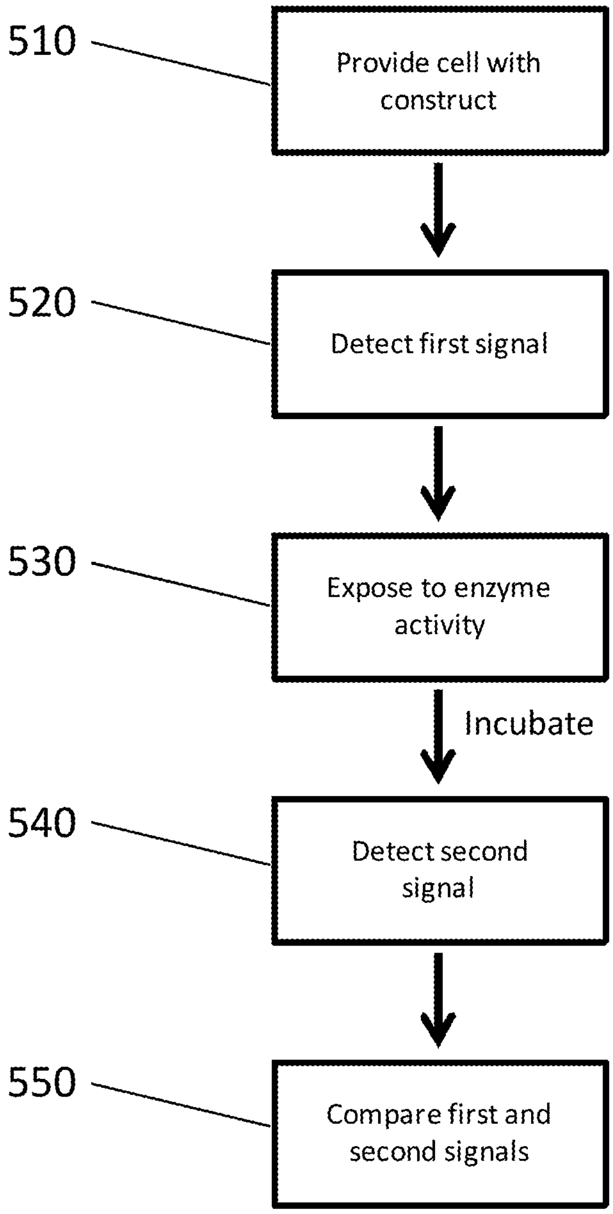
FIG. 5 shows an assay methodology of the invention.

In addition to utilizing different anchoring sites, assays of the inventive concept can use a variety of different testing protocols. One embodiment of such a testing protocol is shown in FIG. 5. Initially 510, a cell is provided that expresses a construct of the inventive concept. A baseline or first signal is acquired 520, then the cell is exposed to the enzyme activity 530. For example, a sample containing an enzyme activity (such as a BoNT) can be added to media containing the cells. After an incubation period a second signal can be detected 540 and subsequently compared to the first signal 550. Such first and second signals can be instant measurements, mean measurements obtained over time, and/or rate measurements.

Figure 6:
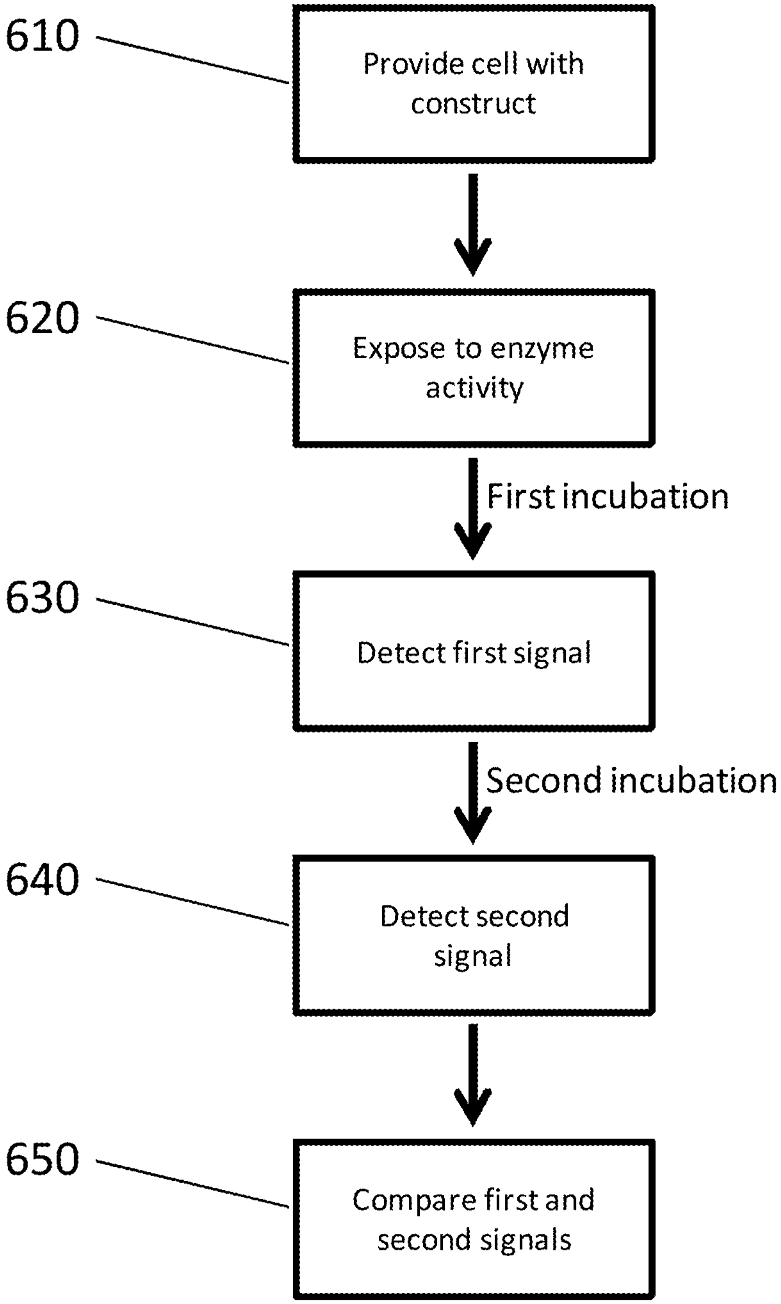
FIG. 6 shows an alternative assay methodology of the invention.

An alternative embodiment of a test method of the inventive concept is shown in FIG. 6. Initially 610, a cell is provided that expresses a construct of the inventive concept. The cell is then exposed to the enzyme activity 620. For example, a sample containing an enzyme activity (such as a BoNT) can be added to media containing the cells. After a first incubation period a baseline or first signal is detected 630 and, following a second incubation period a second signal is detected 640 and subsequently compared to the first signal 650. Such first and second signals can be instant measurements, mean measurements obtained over time, and/or rate measurements.

Figure 7:
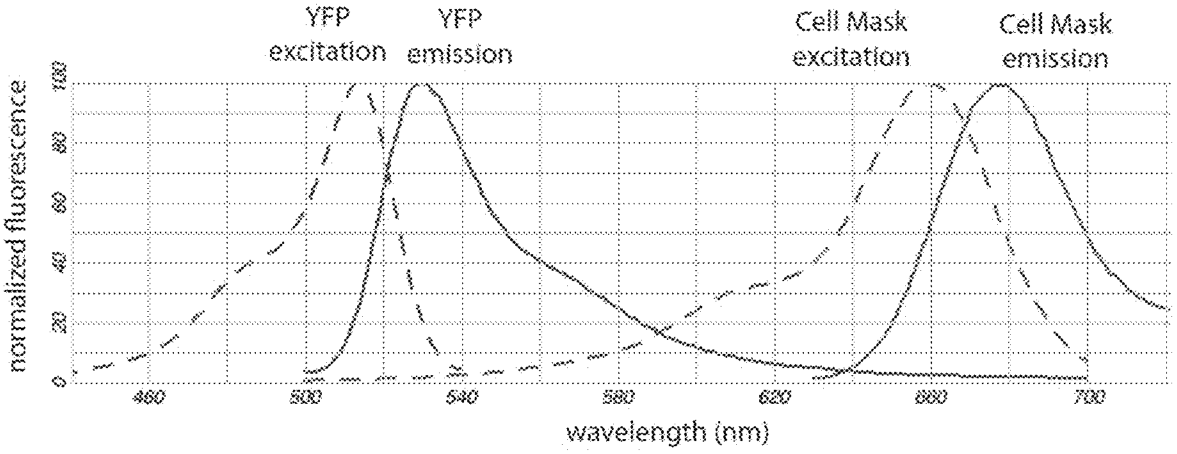
FIG. 7 shows excitation and emission spectra for a fluorescent protein (eYFP) and a secondary dye, FIG. 8 schematically depicts an assay method of the inventive concept that incorporates the use of a secondary dye.

In another embodiment of the inventive concept, cells expressing constructs as described above are exposed to one or more secondary dyes (for example a cell-binding dye such as a membrane dye or a nuclear stain/dye), that are separate from the construct and which can generate signals that are independent of BoNT activity. Such secondary dyes can associate with a membrane and/or nucleus of a cell in a fashion that is independent of the presence of an analyte (for example, a BoNT or other enzyme activity), and can be used to produce a baseline or reference signal, which can be used for normalization. For example, a cell expressing a construct as described above can be exposed to a dye that associates with the nucleus or plasma membrane of the cell, and in turn provides a baseline fluorescent signal. In a preferred embodiment of the inventive concept such a secondary dye is selected such that the emission wavelengths of the membrane dye are distinguishable from those of a reporter fluorophore of the construct expressed in the cells. In some embodiments of the inventive concept the secondary dye can be selected so that the range of effective excitation wavelengths overlaps with those of a reporter fluorophore of the construct, permitting simultaneous excitation of both the secondary dye and the reporter fluorophore and hence simultaneous acquisition of a baseline signal and a reporter fluorophore signal. In other embodiments of the inventive concept a secondary dye can be selected so that the range of effective excitation wavelengths does not overlap significantly with those of the reporter fluorophore, permitting selective excitation of baseline fluorescence. Examples of suitable secondary dyes include 4',6-diamidino-2-phenylindole, dihydrochloride (DAPI), the dye currently known as CELLMASK™ deep red plasma membrane stain, and the nucleus-staining dye currently known as HOECHST3342™. In a preferred embodiment of the inventive concept the secondary dye is selected to provide excitation and emission spectra that have little to no overlap with the excitation and emission spectra of the reporter fluorophore of the construct, such that essentially no (i.e. less than about 5%) energy transfer occurs due to FRET. Examples of excitation and emission spectra of a suitable secondary dye (the dye currently known as CELLMASK™ deep red plasma membrane stain, indicated by "Cell Mask") and a YFP reporter fluorophore are shown in FIG. 7. The inventors contemplate that other suitable secondary dyes can include proteins (for example antibodies) or other macromolecules that have an affinity for the cell and have been conjugated or complexed with fluorescent or other readily detectable molecules.

Since association of secondary dyes with the cells is independent of the presence of the analyte or activity of interest, they can provide a baseline signal that is an independent measure of cell number, density, and/or distribution. Such a baseline signal has considerable utility in normalization of the reporter signal obtained from cells in the course of the performance of an assay of the inventive concept. For example, expressing a result of such an assay as a ratio between the measured reporter signal from a reporter construct that is responsive to the analyte or activity of interest and the measured baseline signal in the form of fluorescence from a membrane dye provides correction for variation in the intensity of the reporter signal from test site to test site due to differences in cell number, density, and/or distribution. This advantageously improves the precision of such assays, which in turn leads to an improvement in effective sensitivity. It should also be appreciated that such a baseline signal can be utilized to provide such normalization for reporter signals other than fluorescence.

EXAMPLE

Figure 8:
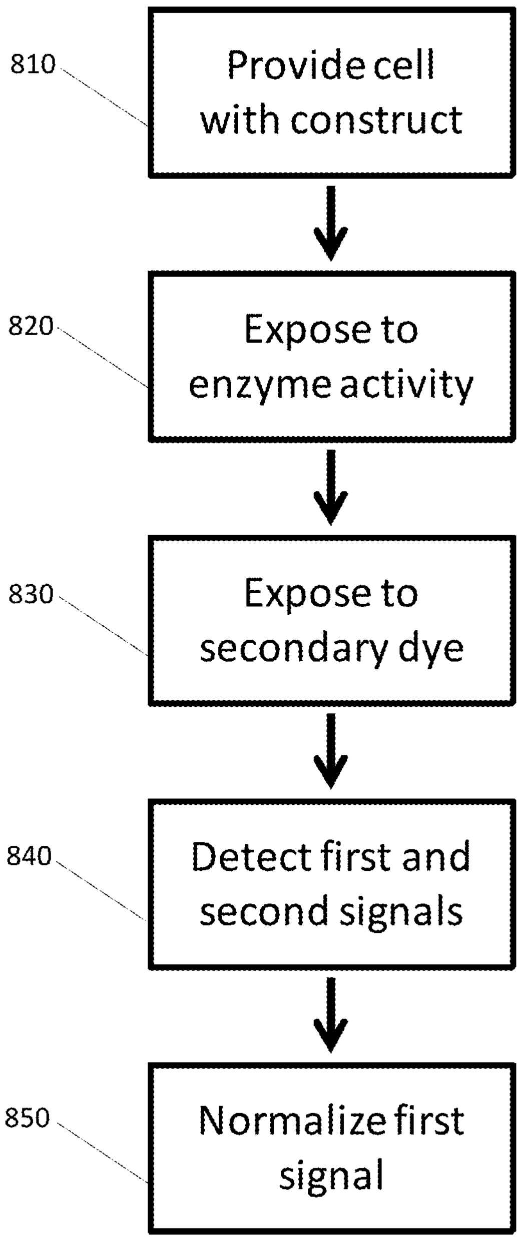

1. As shown schematically in FIG. 8, cells transformed with an expression vector encoding for a construct as described in FIG. 1A are seeded 810 into 96-well plates and incubated overnight at 37° C. with 5% $CO_2$.
2. Cells are then washed with cell culture media and then immediately subjected to BoNT 820 diluted into the cell culture media at 100 µl per well (typically).
3. Cells are then incubated for 48 hours (typically) at 37° C. with 5% $CO_2$.
4. At the end of the 48 hour incubation period, the cells are stained 830 with a secondary dye. Different secondary dyes may be applied using different protocols.

Protocol A: useful for DAPI and the dye currently known as HOECHST3342™.

1. 25 µl of 5 µM DAPI or 25 µg/ml the dye currently known as HOECHST3342™ in cell culture media is added directly to each well of the 96-well plate to give a final concentration of 1 µM DAPI or 5 µg/ml the dye currently known as HOECHST3342™. Useful final concentrations of the nucleus dye range from 0.00110 µM or 0.1-50 µg/ml. Working solution concentrations may be adjusted appropriately.
2. Cells are incubated at 37° C., 5% $CO_2$ for 30 minutes (typically).

Protocol B: useful for the dye currently known as CELLMASK™ deep red plasma membrane stain.

1. A working solution of 0.625-10 µg/ml in Dulbecco's phosphate buffered saline is prepared (5 µg/ml is typical).
2. The BoNT containing cell culture media is removed from each well.
3. 50 µl of the membrane dye working solution is added directly to each well.
4. Cells are incubated at 37° C., 5% $CO_2$ for 20 minutes (typically).

After exposure to the membrane dye, the test plates are washed with phosphate buffered saline using an automated plate washer. The plates are then read on a fluorescence microplate reader using filters with the approximate excitation and emission wavelengths for the fluorophore of the construct and the secondary dye used 840. For example, DAPI and the dye currently known as HOECHST3342™ can be characterized using an excitation wavelength of about 345 nm and an emission wavelength of about 485 nm, while the dye currently known as CELLMASK™ deep red plasma membrane stain can be characterized using an excitation wavelength of about 650 nm and an emission wavelength of about 680 nm. Measurements of the fluorophore of the construct are made independently of those of the membrane dye, using excitation and emission wavelengths characteristic of the fluorophore. For data analysis, directly excited construct fluorophore emission (i.e. the BoNT sensitive component) is normalized 850, for example by dividing the emission of the construct fluorophore by the secondary dye emission (i.e. the BoNT insensitive component).

Figure 9A:
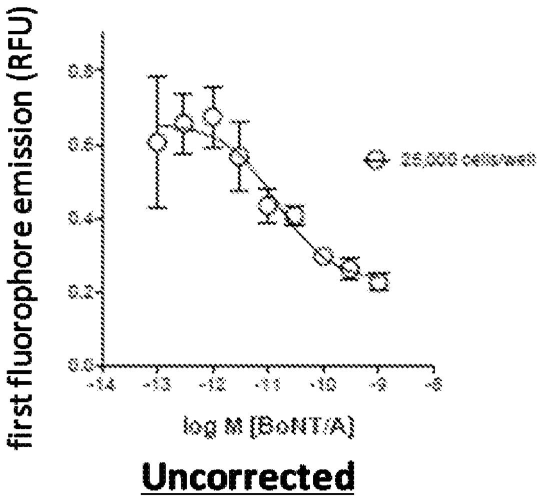
FIG. 9A and 9B show exemplary data from an assay of the inventive concept, using a secondary dye and a reporting construct having SEQ ID NO 14 and representing a construct having the structure shown in FIG. 1A, in the absence of correction and with data normalization, respectively.
Figure 9B:
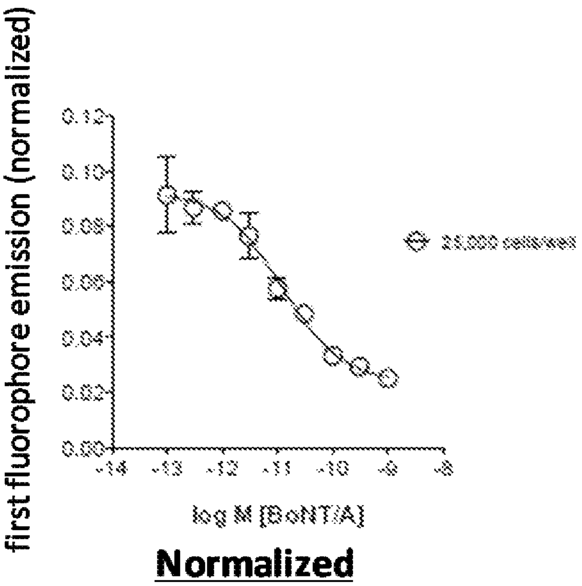
Figure 9C:
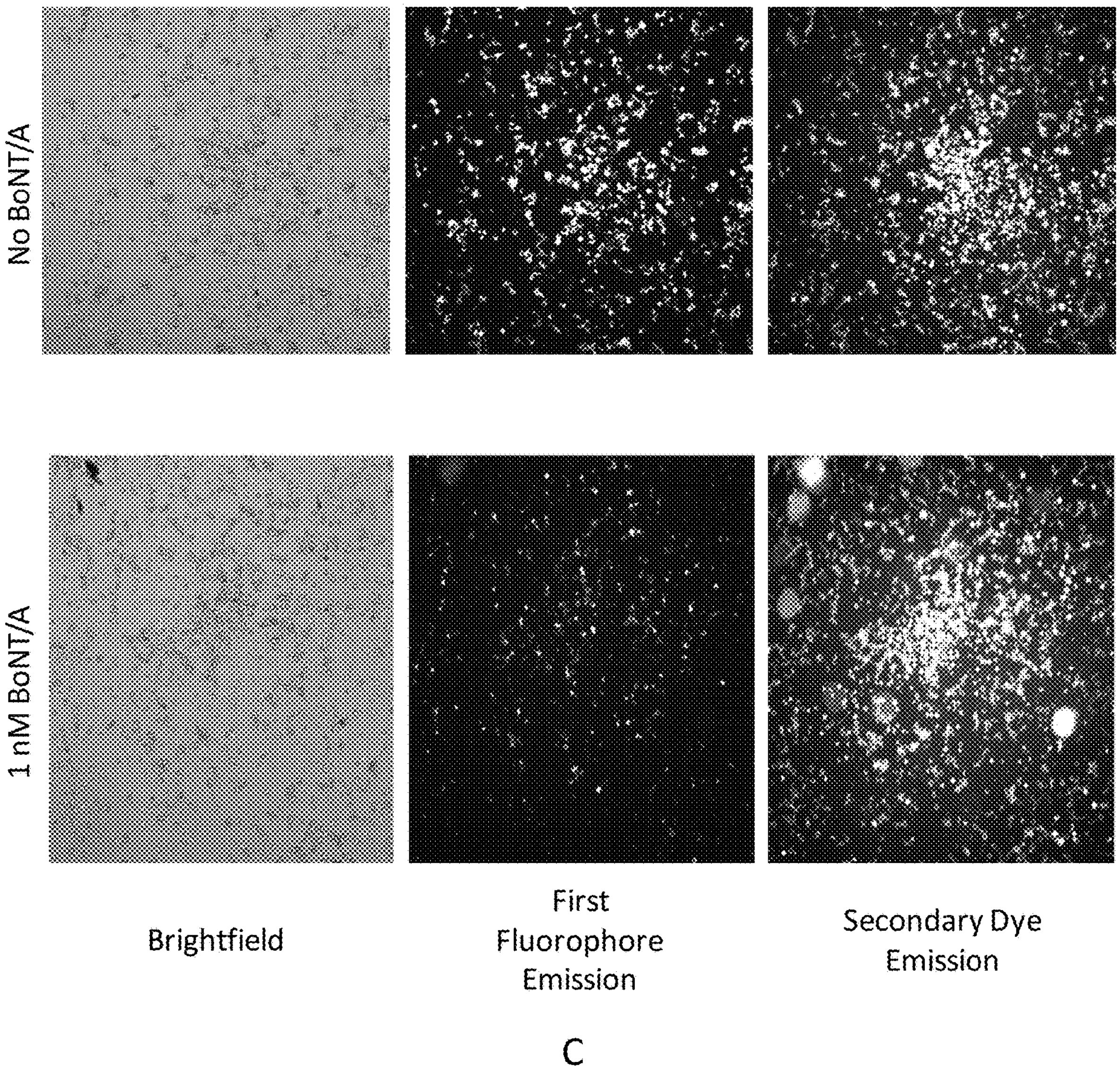
FIG. 9C shows photomicrographs produced using fluorescence and bright field microscopy of cells expressing a construct of the inventive concept, in the absence and in the presence of a corresponding *botulinum* toxin.

Typical results of assays performed with reporting constructs as described above in combination with secondary dyes are shown in FIGS. 9A, 9B, and 9C. FIG. 9A shows typical uncorrected results from contacting cells containing a reporting construct with a protease (in this example, the protease is BoNT/A and the construct includes a cleavage site for BoNT/A. The limit of detection (LOD) in this instance is 10 pM BoNT/A, and the limit of quantitation (LOQ) is 100 pM. FIG. 9B shows the impact of normalization of the fluorescence data from FIG. 9A using emission data from a secondary dye applied to the same cells as described in the above procedure. The LOD for the data shown in FIG. 9B is reduced to 3 pM and the LOQ is reduced to 10 pM. FIG. 9C shows photomicrographs of two wells containing cells having BoNT/A responsive constructs by (from left to right) brightfield, fluorescence microscopy at the emission wavelength of a fluorophore of the construct, and fluorescence microscopy at the emission wavelength of the secondary dye applied to the cells. The well in the upper series of photomicrographs was not exposed to BoNT/A; the well in the lower series of photomicrographs was exposed to 1 nM BoNT/A. The loss of fluorescence from the fluorophore of the construct is evident in the 1 nM BoNT/A well (i.e. the lower series). In contrast, emission from the secondary dye is maintained at a similar, albeit distinct and different, level and distribution from that of the well that was not exposed to BoNT/A (i.e. the upper series)

Variations of these protocols can also be effective. For example, the secondary dyes can be applied prior to contacting the cells with the BoNT, essentially simultaneously with contacting the cells with the BoNT, or at a time interval of less than 48 hours following contacting the cells with the BoNT. Similarly, additional wash steps prior to and following exposure of the cells to the secondary dyes are contemplated.

It should be appreciated that assays of the inventive concept rely on straightforward fluorescence measurements of fluid volumes rather than imaging and/or analysis of individual cells. As such they can be performed using a simple fluorometer (for example, a microplate fluorometer) and are advantageously highly amenable to adaptation to automation and high throughput screening processes. Data analysis is similarly straightforward, as it does not involve processor-intensive image processing tasks such as cell enumeration, identification of individual cells, and the identification of fluorescence localized in specific subcellular regions or compartments.

In addition to providing a baseline signal for data normalization purposes, such secondary dyes can serve other purposes. For example a baseline signal value can be established below which cell numbers are considered insufficient to provide an accurate assay result, permitting data from such a test site to be flagged or discarded. Similarly, a baseline signal value can be established above which cell numbers are considered too high to provide an accurate assay result (for example, due to optical limitations in systems utilized to characterize fluorescence). Inclusion of such secondary dyes with specific reagents that are added during the course of an assay can also be used to verify that such reagents were actually delivered to a test site during the assay process, for example to verify that automated assay systems are performing properly.

In preferred embodiments, the enzyme activity being characterized is associated with *botulinum* toxin, and the cleavage sequence is appropriately matched. Within the context of this application, a BoNT can be defined as a native or modified BoNT that is capable of cleaving a SNARE protein sequence or a portion of a SNARE protein sequence. For example, the BoNT/A, E, and C cleave SNAP-25 and BoNT/B, D, F, G cleaves synaptobrevin (Syb), at single but different sites. BoNT/C also cleaves syntaxin in addition to SNAP-25. Consequently, constructs for the characterization of BoNT/A, E, and C can include cleavage sites sequences that include all or a portion of SNAP-25. Similarly, constructs for the characterization of BoNT B, D, F, and G can include cleavage sites sequences that include all or portions of the respective susceptible regions of synaptobrevin. Alternatively, BoNT/C activity could be characterized utilizing constructs that include cleavage sites with sequences derived from all or part of syntaxin.

Contemplated cleavage site sequences can advantageously comprise a SNARE protein, motif, or mutein. "Muteins" of a protein should be interpreted herein as having at least 30% identity with a corresponding native protein, including for example compositions having at least 35%, 40%, 45%, 50%, 55%, 60%, 65%, 70%, 75%, 80%, 85%, 90%, 95% or 98% identity with the native protein. Variations from identity can comprise any or more of additions, deletions and substitutions. Contemplated muteins include fragments, truncates and fusion proteins.

It is further contemplated that cells of the inventive concept can be modified to express two or more constructs. Such constructs could, for example, be distinguished by the emission spectra of their respective reporters and provide essentially independent and simultaneous measurements of different enzyme activities. Alternatively, such constructs could measure the activities of the same enzyme with different substrate sequences. For example, a first construct could include a cleavage site derived from SNAP-25 and a second construct could include a cleavage site derived from syntaxin, with both being used for characterizing BoNT/C activity. In such an embodiment comparison of the results from both constructs can improve accuracy, dynamic range, and/or specificity.

Another embodiment of the inventive concept is a kit that incorporates a secondary reporter. Such a kit can contain cells that express an appropriate detecting construct, as described above, and a secondary dye (for example, a membrane dye). Optionally, such a kit can include directions for a user to perform the assay. In some embodiments such a kit can include control or calibration materials that include a suitable cell culture media and an enzyme activity corresponding to the enzyme activity of the sample to be characterized. In this context, a control sample is understood to be a sample used to verify assay performance, and a calibration sample is understood to be a sample used to calibrate the output of an assay to provide a quantitative or qualitative result. For example, of a sample suspected of containing a BoNT is to be characterized, such control and/or calibration samples could include a corresponding BoNT. In some embodiments such control and/or calibration samples can be provided pre-mixed and essentially ready for use. In other embodiments (for example, due to stability factors) such control and/or calibrator samples can be provided as a first container of a suitable culture media and a second container of a stock solution of the enzyme activity. In such embodiments the first and second containers may require different shipping and/or storage conditions, and as such may be shipped and/or stored separately while remaining part of the same kit.

Other embodiments of the inventive concept include cell-free assays utilizing the constructs described above. Such an assay could, for example, utilize a cell-free vesicle suspension in which vesicles that carry one or more sites suitable for interacting with a membrane anchoring portion of a construct. Such vesicles, along with a construct of the inventive concept can be suspended in a medium that includes a protease or similar enzyme capable of hydrolyzing a reporter, such that cleavage of a linker portion of the construct would release reporters into the media for hydrolysis. Alternatively, sites recognized by an anchoring portion of a construct can be linked to an appropriately sized microparticle with a suitable surface chemistry. Such microparticles can carry steric blockers, for example high molecular weight dextrans or polyacrylates, that permit *Botulinum* toxins to access the microparticle surface while hindering the access of proteases or similar enzymes. Towards that end, proteases or similar enzymes can be provided in high molecular weight forms (for example, as polymers or as conjugates of high molecular weight molecules) in order to enhance such selectivity.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A reporting construct for performing an assay for a first enzyme activity comprising:

a membrane anchoring domain comprising a first peptide that forms a complex with a membrane of a cell, wherein the cell comprises cytoplasm that includes a protease;

a reporter domain comprising a first occurrence of a second peptide that produces a first signal at a first wavelength and a second occurrence of the second peptide that produces a second signal at the first wavelength, wherein the reporter domain produces an aggregate signal comprising an intensity that is a summation of intensity of the first signal and intensity of the second signal;

a third peptide comprising a cleavage site, the third peptide interposed between the membrane anchoring domain and the reporter domain, wherein the third peptide is selected to undergo a cleavage event at the cleavage site upon exposure to the first enzyme activity, wherein the second peptide is susceptible to proteolysis in cytoplasm of the cell by the protease within a period of time encompassed by the assay, wherein said proteolysis results in an observable reduction in the aggregate signal as a function of the first enzyme activity, and wherein fragmentation of one of the first or second occurrences of the second peptide due to said proteolysis provides a decrease in the aggregate signal wherein the membrane anchoring domain is coupled to an auxiliary reporting domain that provides a signal at a second wavelength, wherein the second wavelength is distinguishable from the first wavelength, and wherein the auxiliary reporting domain remains localized with the cell membrane following the cleavage event.

2. The reporting construct of claim 1, further comprising a linker peptide interposed between the first occurrence of the second peptide and the second occurrence of the second peptide.

3. The reporting construct of claim 1, wherein the third peptide is a SNARE protein or a fragment thereof comprising the cleavage site.

4. The reporting construct of claim 1, wherein the cleavage site is cleaved by the first enzyme activity at a first efficiency characterized by a first $EC_{50}$ and is also susceptible to cleavage by a second enzyme activity at a second efficiency characterized by a second $EC_{50}$, wherein the first $EC_{50}$ and the second $EC_{50}$ are within a factor of 30 of one another.

5. The reporting construct of claim 4, wherein the first enzyme activity is SNAP-25 cleavage by *Botulinum* neurotoxin serotype A and the second enzyme activity is SNAP-25 cleavage by *Botulinum* neurotoxin serotype E, and wherein the reporting construct comprises SEQ ID NO. 14.

6. The reporting construct of claim 1, wherein the reporting construct does not exhibit useful levels of FRET.

7. A method of characterizing a first enzyme activity comprising:

providing a cell that expresses a reporting construct according to claim 1;

contacting the cell with a sample suspected of including the first enzyme activity; and after a time period, observing a decrease in the detectable signal that is proportional to the first enzyme activity, wherein the second peptide is selected to undergo proteolysis in the cell's cytosol within the time period, and wherein the aggregate signal is observable in the absence of either one of the first signal or the second signal.

8. The method of claim 7, wherein the cleavage sites is cleaved by the first enzyme activity at a first efficiency characterized by a first $EC_{50}$ and is also susceptible to cleavage by a second enzyme activity at a second efficiency characterized by a second $EC_{50}$, wherein the first $EC_{50}$ and the second $EC_{50}$ are within a factor of 30 of one another .

9. The method of claim 7 wherein the reporting construct further comprises a reference reporter that produces a reference signal, wherein the reference signal is distinguishable from the detectable signal and is independent of the first enzyme activity.

10. The method of claim 9, comprising a step of applying intensity of the reference signal to normalize intensity the aggregate signal.

11. The method of claim 7, comprising a step of contacting the cell with a cell dye, wherein the cell dye is selected to provide a dye signal that is distinguishable from the aggregate signal.

12. The method of claim 11, wherein the cell is contacted with the cell dye prior to contacting the cell with the sample; or wherein the cell is contacted with the cell dye after the cell is contacted with the sample.

13. The method of claim 11, wherein the cell is contacted with the cell dye and the sample during the same time interval.

* * * * *

SEQUENCE LISTING

```
<160> NUMBER OF SEQ ID NOS: 19

<210> SEQ ID NO 1
<211> LENGTH: 7
<212> TYPE: PRT
<213> ORGANISM: Artificial Sequence
<220> FEATURE:
<223> OTHER INFORMATION: synthetic peptide linker

<400> SEQUENCE: 1

Ser Gly Leu Arg Ser Arg Ala
1               5


<210> SEQ ID NO 2
<211> LENGTH: 4
<212> TYPE: PRT
<213> ORGANISM: Artificial Sequence
<220> FEATURE:
<223> OTHER INFORMATION: synthetic peptide linker

<400> SEQUENCE: 2

Ser Asn Ser Ser
1


<210> SEQ ID NO 3
<211> LENGTH: 6
<212> TYPE: PRT
<213> ORGANISM: Artificial Sequence
<220> FEATURE:
<223> OTHER INFORMATION: synthetic peptide linker

<400> SEQUENCE: 3

Ser Asn Ser Gly Gly Ser
1               5


<210> SEQ ID NO 4
<211> LENGTH: 10
<212> TYPE: PRT
<213> ORGANISM: Artificial Sequence
<220> FEATURE:
<223> OTHER INFORMATION: synthetic peptide linker

<400> SEQUENCE: 4

Gly Gly Gly Gly Ser Gly Gly Gly Gly Ser
1               5                   10


<210> SEQ ID NO 5
<211> LENGTH: 15
<212> TYPE: PRT
<213> ORGANISM: Artificial Sequence
<220> FEATURE:
<223> OTHER INFORMATION: synthetic peptide linker

<400> SEQUENCE: 5

Glu Ala Ala Ala Lys Glu Ala Ala Ala Lys Glu Ala Ala Ala Lys
1               5                   10                  15


<210> SEQ ID NO 6
<211> LENGTH: 6
<212> TYPE: PRT
<213> ORGANISM: Artificial Sequence
<220> FEATURE:
<223> OTHER INFORMATION: synthetic peptide linker

<400> SEQUENCE: 6

Gly Gly Gly Gly Gly Gly
1               5
```

<210> SEQ ID NO 7
<211> LENGTH: 18
<212> TYPE: PRT
<213> ORGANISM: Artificial Sequence
<220> FEATURE:
<223> OTHER INFORMATION: synthetic peptide linker

<400> SEQUENCE: 7

Lys Glu Ser Gly Ser Val Ser Ser Glu Gln Leu Ala Gln Phe Arg Ser
1               5                   10                  15

Leu Asp

<210> SEQ ID NO 8
<211> LENGTH: 14
<212> TYPE: PRT
<213> ORGANISM: Artificial Sequence
<220> FEATURE:
<223> OTHER INFORMATION: synthetic peptide linker

<400> SEQUENCE: 8

Glu Gly Lys Ser Ser Gly Ser Gly Ser Glu Ser Lys Ser Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic peptide linker

<400> SEQUENCE: 9

Gly Ser Ala Gly Ser Ala Ala Gly Ser Gly Glu Phe
1               5                   10

<210> SEQ ID NO 10
<211> LENGTH: 239
<212> TYPE: PRT
<213> ORGANISM: Aequorea victoria

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Gly Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235


<210> SEQ ID NO 11
<211> LENGTH: 247
<212> TYPE: PRT
<213> ORGANISM: Artificial Sequence
<220> FEATURE:
<223> OTHER INFORMATION: green fluorescent protein mutation

<400> SEQUENCE: 11

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Thr Ala Cys Ala Ala Gly Thr
    130                 135                 140

Ala Ala Leu Gly His Lys Leu Glu Tyr Asn Tyr Asn Ser His Asn Val
145                 150                 155                 160

Tyr Ile Met Ala Asp Lys Gln Lys Asn Gly Ile Lys Val Asn Phe Lys
                165                 170                 175

Ile Arg His Asn Ile Glu Asp Gly Ser Val Gln Leu Ala Asp His Tyr
            180                 185                 190

Gln Gln Asn Thr Pro Ile Gly Asp Gly Pro Val Leu Leu Pro Asp Asn
        195                 200                 205

His Tyr Leu Ser Tyr Gln Ser Ala Leu Ser Lys Asp Pro Asn Glu Lys
    210                 215                 220

Arg Asp His Met Val Leu Leu Glu Phe Val Thr Ala Ala Gly Ile Thr
225                 230                 235                 240

Leu Gly Met Asp Glu Leu Tyr
                245


<210> SEQ ID NO 12
<211> LENGTH: 351
<212> TYPE: PRT
<213> ORGANISM: Artificial Sequence
```

-continued

```
<220> FEATURE:
<223> OTHER INFORMATION: green fluorescent protein mutation

<400> SEQUENCE: 12

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Met Ala Glu Asp Ala Asp Met Arg Asn Glu
                245                 250                 255

Leu Glu Glu Met Gln Arg Arg Ala Asp Gln Leu Ala Asp Glu Ser Leu
            260                 265                 270

Glu Ser Thr Arg Arg Met Leu Gln Leu Val Glu Glu Ser Lys Asp Ala
        275                 280                 285

Gly Ile Arg Thr Leu Val Met Leu Cys Phe Pro Asp Glu Gln Gly Glu
    290                 295                 300

Gln Leu Glu Arg Ile Glu Glu Gly Met Asp Gln Ile Asn Lys Asp Met
305                 310                 315                 320

Lys Glu Ala Glu Lys Asn Leu Thr Asp Leu Gly Lys Phe Cys Gly Leu
                325                 330                 335

Cys Val Cys Pro Cys Asn Lys Leu Lys Ser Ser Asp Ala Tyr Lys
            340                 345                 350


<210> SEQ ID NO 13
<211> LENGTH: 248
<212> TYPE: PRT
<213> ORGANISM: Artificial Sequence
<220> FEATURE:
<223> OTHER INFORMATION: green fluroescent protein mutation
```

<400> SEQUENCE: 13

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Trp Ser His Pro Gln Phe Glu Lys
                245

<210> SEQ ID NO 14
<211> LENGTH: 719
<212> TYPE: PRT
<213> ORGANISM: Artificial Sequence
<220> FEATURE:
<223> OTHER INFORMATION: exemplary dual fluorophore construct

<400> SEQUENCE: 14

Ala Ser Ala Thr Met Ala Glu Asp Ala Asp Met Arg Asn Glu Leu Glu
1               5                   10                  15

Glu Met Gln Arg Arg Ala Asp Gln Leu Ala Asp Glu Ser Leu Glu Ser
            20                  25                  30

Thr Arg Arg Met Leu Gln Leu Val Glu Glu Ser Lys Asp Ala Gly Ile
        35                  40                  45

Arg Thr Leu Val Met Leu Asp Glu Gln Gly Glu Gln Leu Glu Arg Ile
    50                  55                  60

Glu Glu Gly Met Asp Gln Ile Asn Lys Asp Met Lys Glu Ala Glu Lys
65                  70                  75                  80

Asn Leu Thr Asp Leu Gly Lys Phe Cys Gly Leu Cys Val Cys Pro Cys
                85                  90                  95

Asn Lys Leu Lys Ser Ser Asp Ala Tyr Lys Lys Ala Trp Gly Asn Asn

-continued 100 105 110

Gln Asp Gly Val Val Ala Ser Gln Pro Ala Arg Val Val Asp Glu Arg
115 120 125

Glu Gln Met Ala Ile Ser Gly Gly Phe Ile Arg Arg Val Thr Asn Asp
130 135 140

Ala Arg Glu Asn Glu Met Asp Glu Asn Leu Glu Gln Val Ser Gly Ile
145 150 155 160

Ile Gly Asn Leu Arg His Met Ala Leu Asp Met Gly Asn Glu Ile Asp
165 170 175

Thr Gln Asn Arg Gln Ile Asp Arg Ile Met Glu Lys Ala Asp Ser Asn
180 185 190

Lys Thr Arg Ile Asp Glu Ala Asn Gln Arg Ala Thr Lys Met Leu Gly
195 200 205

Ser Gly Ser Asn Ser Met Val Ser Lys Gly Glu Glu Leu Phe Thr Gly
210 215 220

Val Val Pro Ile Leu Val Glu Leu Asp Gly Asp Val Asn Gly His Lys
225 230 235 240

Phe Ser Val Ser Gly Glu Gly Glu Gly Asp Ala Thr Tyr Gly Lys Leu
245 250 255

Thr Leu Lys Phe Ile Cys Thr Thr Gly Lys Leu Pro Val Pro Trp Pro
260 265 270

Thr Leu Val Thr Thr Phe Gly Tyr Gly Leu Gln Cys Phe Ala Arg Tyr
275 280 285

Pro Asp His Met Lys Gln His Asp Phe Phe Lys Ser Ala Met Pro Glu
290 295 300

Gly Tyr Val Gln Glu Arg Thr Ile Phe Phe Lys Asp Asp Gly Asn Tyr
305 310 315 320

Lys Thr Arg Ala Glu Val Lys Phe Glu Gly Asp Thr Leu Val Asn Arg
325 330 335

Ile Glu Leu Lys Gly Ile Asp Phe Lys Glu Asp Gly Asn Ile Leu Gly
340 345 350

His Lys Leu Glu Tyr Asn Tyr Asn Ser His Asn Val Tyr Ile Met Ala
355 360 365

Asp Lys Gln Lys Asn Gly Ile Lys Val Asn Phe Lys Ile Arg His Asn
370 375 380

Ile Glu Asp Gly Ser Val Gln Leu Ala Asp His Tyr Gln Gln Asn Thr
385 390 395 400

Pro Ile Gly Asp Gly Pro Val Leu Leu Pro Asp Asn His Tyr Leu Ser
405 410 415

Tyr Gln Ser Ala Leu Ser Lys Asp Pro Asn Glu Lys Arg Asp His Met
420 425 430

Val Leu Leu Glu Phe Val Thr Ala Ala Gly Ile Thr Leu Gly Met Asp
435 440 445

Glu Leu Tyr Lys Leu Glu Gly Gly Gly Gly Ser Gly Gly Gly Gly Ser
450 455 460

Met Val Ser Lys Gly Glu Glu Leu Phe Thr Gly Val Val Pro Ile Leu
465 470 475 480

Val Glu Leu Asp Gly Asp Val Asn Gly His Lys Phe Ser Val Ser Gly
485 490 495

Glu Gly Glu Gly Asp Ala Thr Tyr Gly Lys Leu Thr Leu Lys Phe Ile
500 505 510

Cys Thr Thr Gly Lys Leu Pro Val Pro Trp Pro Thr Leu Val Thr Thr
515 520 525

-continued

```
Phe Gly Tyr Gly Leu Gln Cys Phe Ala Arg Tyr Pro Asp His Met Lys
    530                 535                 540

Gln His Asp Phe Phe Lys Ser Ala Met Pro Glu Gly Tyr Val Gln Glu
545                 550                 555                 560

Arg Thr Ile Phe Phe Lys Asp Asp Gly Asn Tyr Lys Thr Arg Ala Glu
                565                 570                 575

Val Lys Phe Glu Gly Asp Thr Leu Val Asn Arg Ile Glu Leu Lys Gly
            580                 585                 590

Ile Asp Phe Lys Glu Asp Gly Asn Ile Leu Gly His Lys Leu Glu Tyr
        595                 600                 605

Asn Tyr Asn Ser His Asn Val Tyr Ile Met Ala Asp Lys Gln Lys Asn
    610                 615                 620

Gly Ile Lys Val Asn Phe Lys Ile Arg His Asn Ile Glu Asp Gly Ser
625                 630                 635                 640

Val Gln Leu Ala Asp His Tyr Gln Gln Asn Thr Pro Ile Gly Asp Gly
                645                 650                 655

Pro Val Leu Leu Pro Asp Asn His Tyr Leu Ser Tyr Gln Ser Ala Leu
            660                 665                 670

Ser Lys Asp Pro Asn Glu Lys Arg Asp His Met Val Leu Leu Glu Phe
        675                 680                 685

Val Thr Ala Ala Gly Ile Thr Leu Gly Met Asp Glu Leu Tyr Lys Gly
    690                 695                 700

Gly Gly Gly Ser Tyr Pro Tyr Asp Val Pro Asp Tyr Ala Gly Thr
705                 710                 715


<210> SEQ ID NO 15
<211> LENGTH: 205
<212> TYPE: PRT
<213> ORGANISM: Mus musculus

<400> SEQUENCE: 15

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Met Lys Glu Ala Glu Lys Asn Leu Thr Asp Leu
65                  70                  75                  80

Gly Lys Phe Cys Gly Leu Cys Val Cys Pro Cys Asn Lys Leu Lys Ser
                85                  90                  95

Ser Asp Ala Tyr Lys Lys Ala Trp Gly Asn Asn Gln Asp Gly Val Val
            100                 105                 110

Ala Ser Gln Pro Ala Arg Val Val Asp Glu Arg Glu Gln Met Ala Ile
        115                 120                 125

Ser Gly Gly Phe Ile Arg Arg Val Thr Asn Asp Ala Arg Glu Asn Glu
    130                 135                 140

Met Asp Glu Asn Leu Glu Gln Val Ser Gly Ile Ile Gly Asn Leu Arg
145                 150                 155                 160

His Met Ala Leu Asp Met Gly Asn Glu Ile Asp Thr Gln Asn Arg Gln
                165                 170                 175

Ile Asp Arg Ile Met Glu Lys Ala Asp Ser Asn Lys Thr Arg Ile Asp
```

```
            180                 185                 190

Glu Ala Asn Gln Arg Ala Thr Lys Met Leu Gly Ser Gly
        195                 200                 205


<210> SEQ ID NO 16
<211> LENGTH: 66
<212> TYPE: PRT
<213> ORGANISM: Artificial Sequence
<220> FEATURE:
<223> OTHER INFORMATION: SNAP-25 fragment

<400> SEQUENCE: 16

Ala Arg Glu Asn Glu Met Asp Glu Asn Leu Glu Gln Val Ser Gly Ile
1               5                   10                  15

Ile Gly Asn Leu Arg His Met Ala Leu Asp Met Gly Asn Glu Ile Asp
            20                  25                  30

Thr Gln Asn Arg Gln Ile Asp Arg Ile Met Glu Lys Ala Asp Ser Asn
        35                  40                  45

Lys Thr Arg Ile Asp Glu Ala Asn Gln Arg Ala Thr Lys Met Leu Gly
    50                  55                  60

Ser Gly
65


<210> SEQ ID NO 17
<211> LENGTH: 116
<212> TYPE: PRT
<213> ORGANISM: Rattus norvegicus

<400> SEQUENCE: 17

Met Ser Ala Thr Ala Ala Thr Ala Pro Pro Ala Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115


<210> SEQ ID NO 18
<211> LENGTH: 63
<212> TYPE: PRT
<213> ORGANISM: Artificial Sequence
<220> FEATURE:
<223> OTHER INFORMATION: synaptobrevin fragment

<400> SEQUENCE: 18

Gln Gln Thr Gln Ala Gln Val Asp Glu Val Val Asp Ile Met Arg Val
1               5                   10                  15

Asn Val Asp Lys Val Leu Glu Arg Asp Gln Lys Leu Ser Glu Leu Asp
            20                  25                  30

Asp Arg Ala Asp Ala Leu Gln Ala Gly Ala Ser Gln Phe Glu Thr Ser
```

```
        35                  40                  45

Ala Ala Lys Leu Lys Arg Lys Tyr Trp Trp Lys Asn Leu Lys Met
    50                  55                  60


<210> SEQ ID NO 19
<211> LENGTH: 706
<212> TYPE: PRT
<213> ORGANISM: Artificial Sequence
<220> FEATURE:
<223> OTHER INFORMATION: Amino acid sequence for BoCell A reporting
      construct, having a single fluorescent peptide sequence in the
      reporter domain

<400> SEQUENCE: 19

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Met Ala Glu Asp Ala Asp Met Arg Asn Glu
                245                 250                 255

Leu Glu Glu Met Gln Arg Arg Ala Asp Gln Leu Ala Asp Glu Ser Leu
            260                 265                 270

Glu Ser Thr Arg Arg Met Leu Gln Leu Val Glu Glu Ser Lys Asp Ala
        275                 280                 285

Gly Ile Arg Thr Leu Val Met Leu Cys Phe Pro Asp Glu Gln Gly Glu
    290                 295                 300

Gln Leu Glu Arg Ile Glu Glu Gly Met Asp Gln Ile Asn Lys Asp Met
305                 310                 315                 320

Lys Glu Ala Glu Lys Asn Leu Thr Asp Leu Gly Lys Phe Cys Gly Leu
                325                 330                 335
```

-continued

```
Cys Val Cys Pro Cys Asn Lys Leu Lys Ser Ser Asp Ala Tyr Lys Lys
            340                 345                 350

Ala Trp Gly Asn Asn Gln Asp Gly Val Val Ala Ser Gln Pro Ala Arg
        355                 360                 365

Val Val Asp Glu Arg Glu Gln Met Ala Ile Ser Gly Gly Phe Ile Arg
    370                 375                 380

Arg Val Thr Asn Asp Ala Arg Glu Asn Glu Met Asp Glu Asn Leu Glu
385                 390                 395                 400

Gln Val Ser Gly Ile Ile Gly Asn Leu Arg His Met Ala Leu Asp Met
                405                 410                 415

Gly Asn Glu Ile Asp Thr Gln Asn Arg Gln Ile Asp Arg Ile Met Glu
            420                 425                 430

Lys Ala Asp Ser Asn Lys Thr Arg Ile Asp Glu Ala Asn Gln Arg Ala
        435                 440                 445

Thr Lys Met Leu Gly Ser Gly Ser Asn Ser Met Val Ser Lys Gly Glu
    450                 455                 460

Glu Leu Phe Thr Gly Val Val Pro Ile Leu Val Glu Leu Asp Gly Asp
465                 470                 475                 480

Val Asn Gly His Lys Phe Ser Val Ser Gly Glu Gly Glu Gly Asp Ala
                485                 490                 495

Thr Tyr Gly Lys Leu Thr Leu Lys Phe Ile Cys Thr Thr Gly Lys Leu
            500                 505                 510

Pro Val Pro Trp Pro Thr Leu Val Thr Thr Phe Gly Tyr Gly Leu Gln
        515                 520                 525

Cys Phe Ala Arg Tyr Pro Asp His Met Lys Gln His Asp Phe Phe Lys
    530                 535                 540

Ser Ala Met Pro Glu Gly Tyr Val Gln Glu Arg Thr Ile Phe Phe Lys
545                 550                 555                 560

Asp Asp Gly Asn Tyr Lys Thr Arg Ala Glu Val Lys Phe Glu Gly Asp
                565                 570                 575

Thr Leu Val Asn Arg Ile Glu Leu Lys Gly Ile Asp Phe Lys Glu Asp
            580                 585                 590

Gly Asn Ile Thr Ala Cys Ala Ala Gly Thr Ala Ala Leu Gly His Lys
        595                 600                 605

Leu Glu Tyr Asn Tyr Asn Ser His Asn Val Tyr Ile Met Ala Asp Lys
    610                 615                 620

Gln Lys Asn Gly Ile Lys Val Asn Phe Lys Ile Arg His Asn Ile Glu
625                 630                 635                 640

Asp Gly Ser Val Gln Leu Ala Asp His Tyr Gln Gln Asn Thr Pro Ile
                645                 650                 655

Gly Asp Gly Pro Val Leu Leu Pro Asp Asn His Tyr Leu Ser Tyr Gln
            660                 665                 670

Ser Ala Leu Ser Lys Asp Pro Asn Glu Lys Arg Asp His Met Val Leu
        675                 680                 685

Leu Glu Phe Val Thr Ala Ala Gly Ile Thr Leu Gly Met Asp Glu Leu
    690                 695                 700

Tyr Lys
705
```